(12) United States Patent
Stephenson et al.

(10) Patent No.: US 12,089,009 B2
(45) Date of Patent: Sep. 10, 2024

(54) HEARING AID DEVICE WITH BIOMETRIC SENSOR

(71) Applicant: YUKKA MAGIC LLC, Wilmington, DE (US)

(72) Inventors: Shawn M. Stephenson, Raleigh, NC (US); Aart Zeger Van Halteren, Hoofddorp (NL); Peter Christiaan Post, Hoofddorp (NL); Aster Katoen, Hoofddorp (NL); Dennis Mocking, Hoofddorp (NL); Alwin Fransen, Hoofddorp (NL)

(73) Assignee: YUKKA MAGIC LLC, Wilmington, DE (US)

( * ) Notice: Subject to any disclaimer, the term of this patent is extended or adjusted under 35 U.S.C. 154(b) by 641 days.

(21) Appl. No.: 17/268,026

(22) PCT Filed: Sep. 16, 2019

(86) PCT No.: PCT/US2019/051263
§ 371 (c)(1),
(2) Date: Feb. 11, 2021

(87) PCT Pub. No.: WO2020/060911
PCT Pub. Date: Mar. 26, 2020

(65) Prior Publication Data
US 2021/0168539 A1 Jun. 3, 2021

Related U.S. Application Data

(60) Provisional application No. 62/733,327, filed on Sep. 19, 2018.

(51) Int. Cl.
*H04R 25/00* (2006.01)
*A61B 5/00* (2006.01)
(Continued)

(52) U.S. Cl.
CPC ......... *H04R 25/603* (2019.05); *A61B 5/0205* (2013.01); *A61B 5/1455* (2013.01);
(Continued)

(58) Field of Classification Search
CPC .. H04R 1/1016; H04R 1/1091; H04R 23/008; H04R 25/603; H04R 25/65;
(Continued)

(56) References Cited

U.S. PATENT DOCUMENTS 11,589,812 B2 * 2/2023 LeBoeuf .............. A61B 5/6803
2006/0107744 A1 5/2006 Li et al.
(Continued)

OTHER PUBLICATIONS

"International Search Report and Written Opinion of the International Searching Authority", International Application No. PCT/US2019/051263, Dec. 4, 2019, 10 pp.

*Primary Examiner* — Huyen D Le
(74) *Attorney, Agent, or Firm* — Brownstein Hyatt Farber Schreck, LLP

(57) ABSTRACT

A hearing aid module includes an elongated housing, an optical sensor module within the housing, an audio driver positioned within the housing adjacent the optical sensor module, and first and second light guides positioned near the audio driver. The module has a rectangular configuration with opposite first and second sides, opposite third and fourth sides, and opposite first and second ends. The first and second sides each include an opening. An ear tip is coupled to the housing first end and is configured to retain the module within the auditory canal. The first light guide guides light from an optical emitter through the opening in the housing first side and into skin of the auditory canal in a non-line of sight manner. The second light guide collects light from the skin of the auditory canal and directs the collected light to an optical detector in a non-line of sight manner.

19 Claims, 23 Drawing Sheets

(51) Int. Cl.
  *A61B 5/0205*   (2006.01)
  *A61B 5/1455*   (2006.01)
  *H04R 1/10*     (2006.01)
  *H04R 23/00*    (2006.01)

(52) U.S. Cl.
  CPC .......... *A61B 5/6803* (2013.01); *A61B 5/6815* (2013.01); *H04R 1/1016* (2013.01); *H04R 23/008* (2013.01); *H04R 25/65* (2013.01); *A61B 2560/0242* (2013.01); *A61B 2562/0238* (2013.01); *H04R 2225/0216* (2019.05)

(58) Field of Classification Search
  CPC .... H04R 2225/0216; A61B 2562/0238; A61B 5/1455; A61B 5/6803; A61B 5/6815; A61B 2562/0233
  See application file for complete search history.

(56) References Cited

U.S. PATENT DOCUMENTS

| | | |
|---|---|---|
| 2014/0254846 A1 | 9/2014 | Wagner et al. |
| 2017/0119315 A1 | 5/2017 | Leboeuf et al. |
| 2018/0042554 A1 | 2/2018 | Wagner et al. |
| 2018/0063621 A1 | 3/2018 | Qian et al. |
| 2021/0038161 A1* | 2/2021 | Stephenson .......... A61B 5/0059 |
| 2021/0298619 A1* | 9/2021 | Stephenson ........ A61B 5/02416 |

* cited by examiner

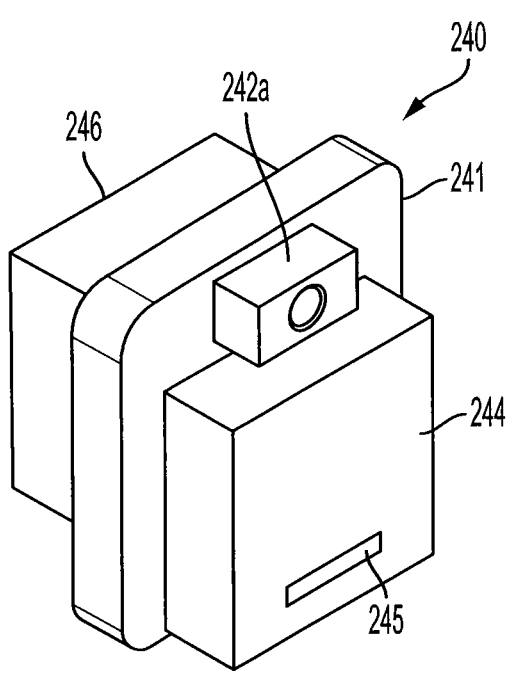
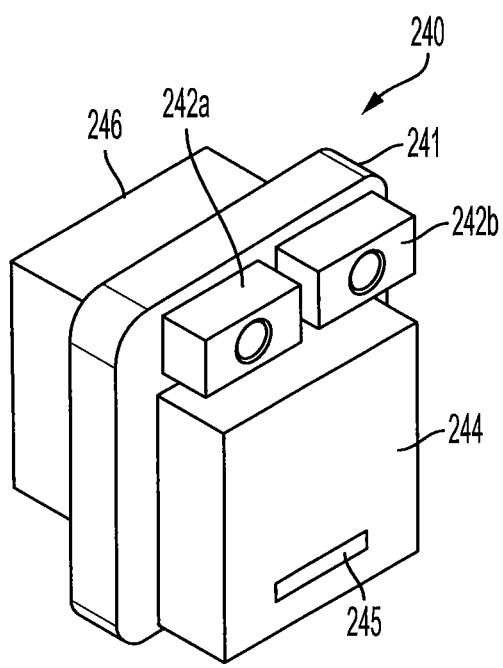
FIG. 11A  FIG. 11B
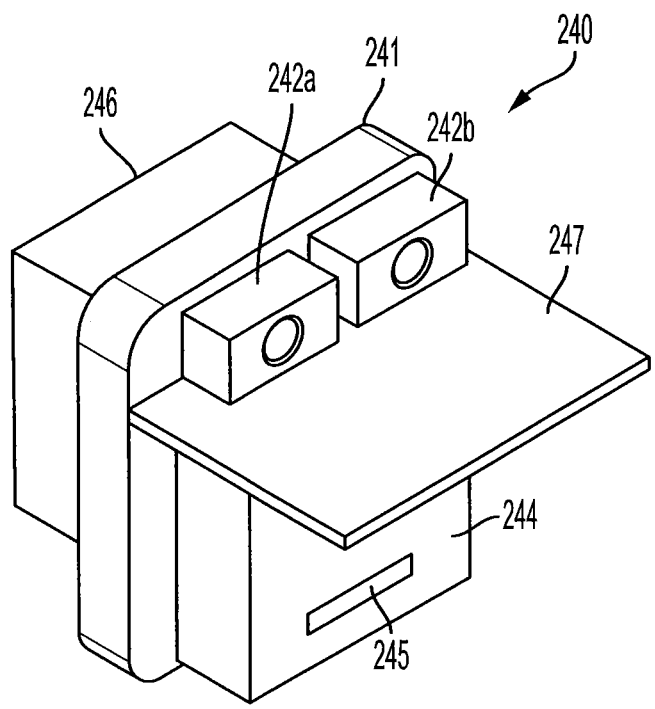
FIG. 12

HEARING AID DEVICE WITH BIOMETRIC SENSOR

RELATED APPLICATIONS

This application is a 35 U.S.C. § 371 national stage application of PCT Application No. PCT/US2019/051263, filed Sep. 16, 2019, which itself claims the benefit of and priority to U.S. Provisional Patent Application No. 62/733,327 filed Sep. 19, 2018, the disclosures of both which are incorporated herein by reference as if set forth in their entireties. The above-referenced PCT International Application was published in the English language as International Publication No. WO 2020/060911 A1 on Mar. 26, 2020.

FIELD OF THE INVENTION

The present invention relates generally to monitoring devices and, more particularly, to optical sensor devices.

BACKGROUND OF THE INVENTION

There is growing market demand for personal health and environmental monitors, for example, for gauging overall health and metabolism during exercise, athletic training, dieting, daily life activities, sickness, and physical therapy. However, traditional health monitors and environmental monitors may be bulky, rigid, and uncomfortable—generally not suitable for use during daily physical activity.

FIGS. 1A-1B and 2 illustrate a prior art ear worn fitness tracking device 10 having a biometric sensor assembly 12 and a speaker 14 in different locations. In FIG. 1B the housing of the device 10 is transparent to better illustrate the location of the biometric sensor assembly 12 and speaker 14. As illustrated in FIG. 2, when the device 10 of FIGS. 1A-1B is worn, the housing of the device 10 generally fills the volume of the Concha Cavum and both the biometric sensor assembly 12 and speaker 14 are located outside of the auditory canal. The addition of the biometric sensor assembly 12 to the device 10 creates challenges to user comfort as well as to perceived overall size of the device 10.

Referring to FIGS. 3A-3B, the biometric sensor assembly 12 of the device 10 of FIGS. 1A-1B is illustrated. The illustrated biometric sensor assembly 12 includes a housing 16 having windows 18 formed therein. A printed circuit board 20 supporting an optical emitter 22 and optical detector 24 and related electronics is secured to the housing 16. Light guides 26 are positioned within the windows 18 and are configured to guide light from the optical emitter through a respective window 18 and collect light through a respective window 18 and guide the collected light to the optical detector 24.

In addition, other wearable fitness trackers are focused on wrist-worn form-factors that are used for sports and fitness applications rather than form-factors routinely used by those having health conditions.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a hearing aid module configured to be inserted within the auditory canal of an ear of a subject includes an elongated housing, an optical sensor module positioned within the housing, an audio driver positioned within the housing adjacent the optical sensor module that is configured to provide sound to the subject, and first and second light guides. One or both of the first and second light guides may be supported by the audio driver in some embodiments. However, in other embodiments, one or both of the first and second light guides may be supported by the housing or one or more other components and do not contact the audio driver.

The module has a rectangular configuration with opposite first and second sides, opposite third and fourth sides, and opposite first and second ends. The first and second sides each include an opening, and an acoustic passage is formed through the housing first end. An ear tip is coupled to the housing at the first end and is configured to retain the module within the auditory canal.

In some embodiments, the housing includes front and rear sections that are joined together. In some embodiments, portions of the housing adjacent the first opening and/or the second opening are opaque.

The optical sensor module includes at least one optical emitter and at least one optical detector. The first light guide is configured to guide light from the at least one optical emitter through the opening in the housing first side and toward the skin of the auditory canal in a non-line of sight manner. The second light guide is configured to collect light from the skin of the auditory canal and direct the collected light to the at least one optical detector in a non-line of sight manner.

The module may include an opaque barrier or body positioned between the optical sensor module and the audio driver to prevent crosstalk between the at least one optical emitter and the at least one optical detector. In some embodiments, the opaque body has opposite first and second sides, opposite third and fourth sides, and opposite first and second end portions. The opaque body first end portion abuts the optical sensor module or is in close relationship thereto, the opaque body second end portion abuts an end portion of the audio driver or is in close relationship thereto, the opaque body first side abuts a portion of the first light guide or is in close relationship thereto, and the opaque body second side abuts a portion of the second light guide or is in close relationship thereto. In other embodiments, the opaque body may be a part of a housing of the audio driver.

The first light guide includes first and second sections. The first section has an elongated flat configuration with opposite first and second ends and opposite first and second surfaces. The second section extends outwardly from the second surface of the first section adjacent the first end of the first section. The second section is positioned near the at least one optical emitter and the first section second surface abuts or is located very close to a surface of the audio driver. Light from the at least one optical emitter passes into the first light guide through the second section and exits through the first section first surface.

The second light guide includes first and second sections. The first section has an elongated flat configuration with opposite first and second ends and opposite first and second surfaces. The second section extends outwardly from the second surface of the first section adjacent the first end of the first section. The second section is positioned near the at least one optical detector and the first section second surface abuts or is located very close to a surface of the audio driver. The second light guide collects light from the skin of the auditory canal through the first section first surface and directs the collected light into the at least one optical detector via the second section.

According to some embodiments of the present invention, a hearing aid device includes a first module comprising a power supply and a second module as described above configured to be inserted within an auditory canal of an ear of a subject. The first and second modules are electrically coupled via a cable.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate various embodiments of the present invention. The drawings and description together serve to fully explain embodiments of the present invention.

In FIG. 6B, the housing of the RIC module is transparent to illustrate the components therewithin.

FIG. 11A is a front perspective view of an optical sensor module having a printed circuit board supporting an optical emitter and detector on one side and an accelerometer on the opposite, side according to some embodiments of the present invention.

FIG. 11B is a front perspective view of an optical sensor module having a printed circuit board supporting two optical emitters and an optical detector on one side and an accelerometer on the opposite side, according to other embodiments of the present invention.

FIG. 12 illustrates the optical sensor module of FIG. 11B with an opaque barrier positioned between the optical emitters and the optical detector to prevent crosstalk therebetween, according to some embodiments of the present invention.

DETAILED DESCRIPTION

Figure 1A:
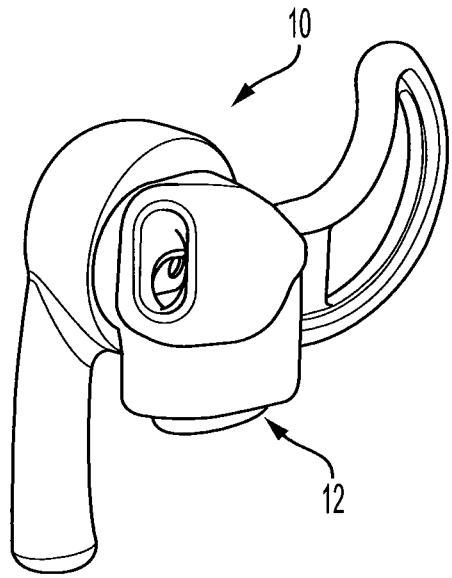
FIGS. 1A-1B illustrate a prior art ear worn fitness tracking device.
Figure 1B:
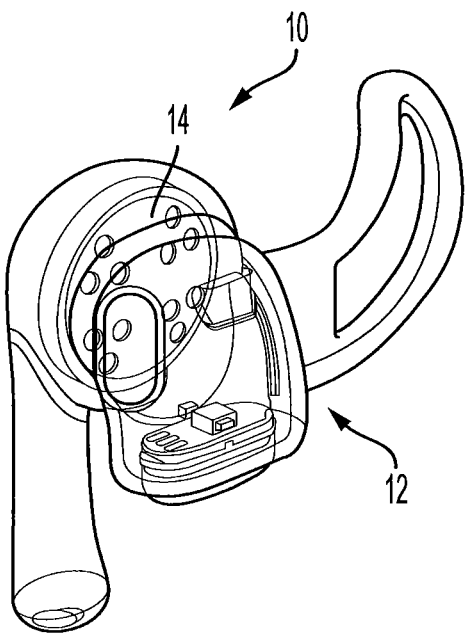
Figure 2:
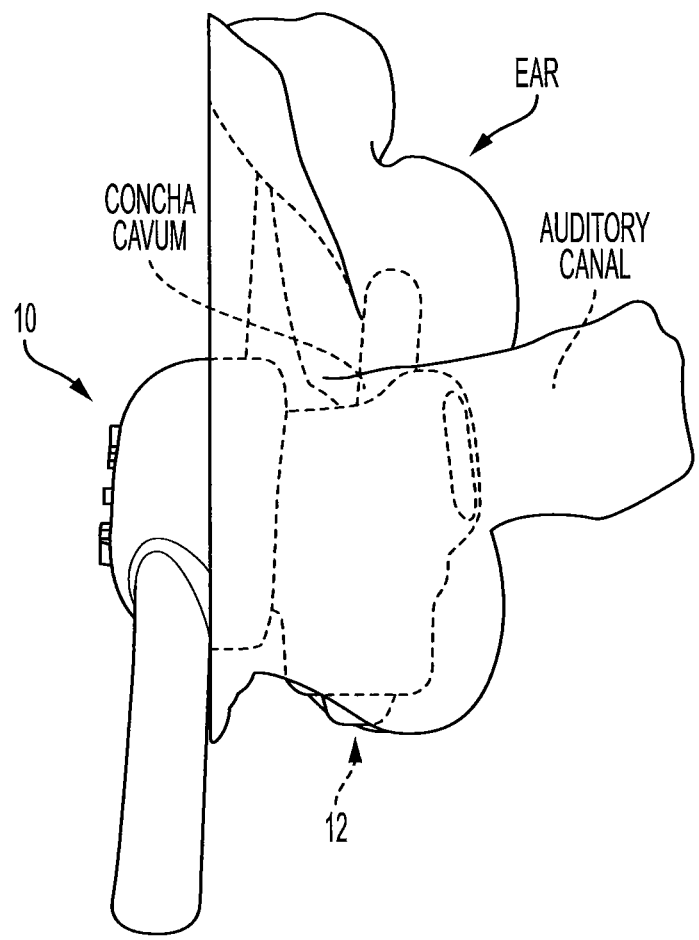
FIG. 2 illustrates the device of FIGS. 1A-1B inserted within the ear of a person.
Figure 3A:
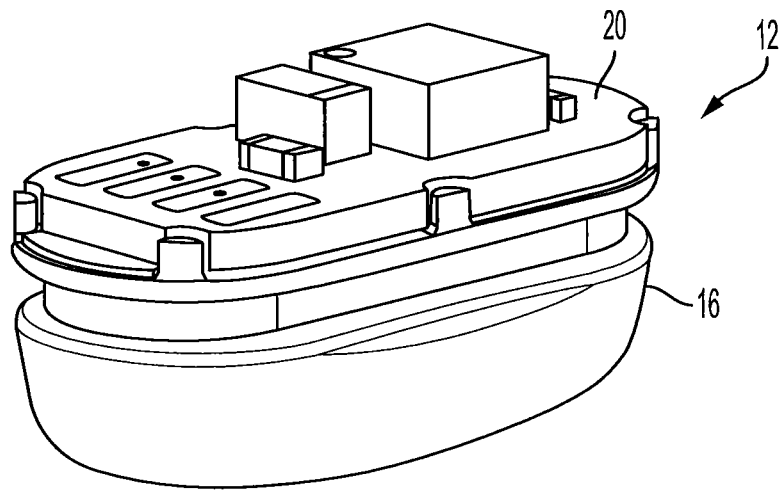
FIG. 3A is a bottom perspective view of the biometric sensor assembly of the device of FIGS. 1A-1B.
Figure 3B:
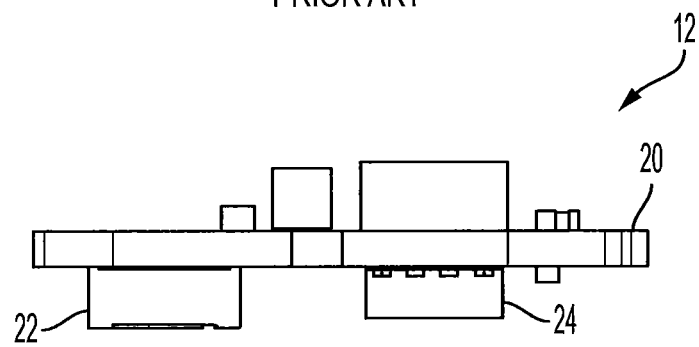
FIG. 3B is an exploded side view of the biometric sensor assembly of FIG. 3A.
Figure 3B:
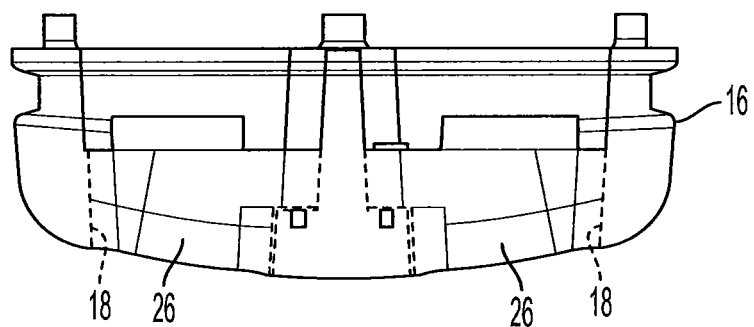

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled", or "secured" to another feature or element, it can be directly connected, attached, coupled, or secured to the other feature or element or intervening features or elements may be present. In contrast, when a feature or element is referred to as being "directly connected", "directly attached", "directly coupled", or "directly secured" to another feature or element, there are no intervening features or elements present. Although described or shown with respect to one embodiment, the features and elements so described or shown can apply to other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

As used herein, the term "and/or" includes any and all combinations of one or more of the associated listed items and may be abbreviated as "/".

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various features or elements, these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "about", as used herein with respect to a value or number, means that the value or number can vary, for example, by as much as +/−20%.

The terms "optical source" and "optical emitter", as used herein, are interchangeable.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" may include monitoring blood gas levels, blood hydration, and metabolite/electrolyte levels, etc.

The term "physiological" refers to matter or energy of or from the body of a creature (e.g., humans, animals, etc.). In embodiments of the present invention, the term "physiological" is intended to be used broadly, covering both physical and psychological matter and energy of or from the body of a creature. However, in some cases, the term "psychological" is called-out separately to emphasize aspects of physiology that are more closely tied to conscious or subconscious brain activity rather than the activity of other organs, tissues, or cells.

The term "body" refers to the body of a subject (human or animal) that may wear a device incorporating one or more optical sensor modules, according to embodiments of the present invention.

The term "coupling", as used herein, refers to the interaction or communication between excitation energy entering a region of a body and the region itself. For example, one form of optical coupling may be the interaction between excitation light generated from an optical sensor module and the blood vessels of the body of a user. In one embodiment, this interaction may involve excitation light entering the ear region and scattering from a blood vessel in the ear such that the intensity of scattered light is proportional to blood flow within the blood vessel.

The term "processor" is used broadly to refer to a signal processor or computing system or processing or computing method which may be localized or distributed. For example, a localized signal processor may comprise one or more signal processors or processing methods localized to a general location, such as to an earbud. Examples of a distributed processor include "the cloud", the internet, a remote database, a remote processor computer, a plurality of remote processors or computers in communication with each other, or the like, or processing methods distributed amongst one or more of these elements. The key difference is that a distributed processor may include delocalized elements, whereas a localized processor may work independently of a distributed processing system. Microprocessors, microcontrollers, ASICs (application specific integrated circuits), analog processing circuitry, made-for AI (artificial intelligence) circuitry, and digital signal processors are a few non-limiting examples of physical signal processors that may be found in wearable devices.

The term "remote" does not necessarily mean that a remote device is a wireless device or that it is a long distance away from a device in communication therewith. Rather, the term "remote" is intended to reference a device or system that is distinct from another device or system or that is not substantially reliant on another device or system for core functionality. For example, a computer wired to a wearable device may be considered a remote device, as the two devices are distinct and/or not substantially reliant on each other for core functionality. However, any wireless device (such as a portable device, for example) or system (such as a remote database for example) is considered remote to any other wireless device or system.

Figure 4:
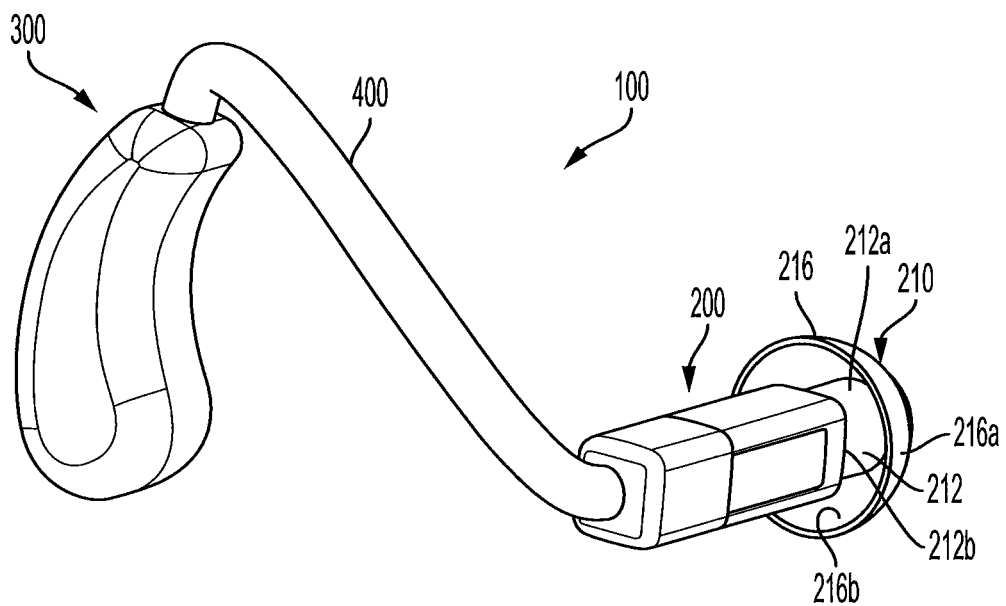
FIG. 4 is a perspective view of a hearing aid device according to some embodiments of the present invention.

Referring now to the drawings, some embodiments of the present invention are illustrated. FIG. 4 illustrates a hearing aid device 100 having a receiver-in-ear ("RIC") module 200 connected to a behind-the-ear ("BTE") module 300 by cable 400. In some embodiments, the BTE module 300 is adapted to be disposed behind an ear of a user during operation of the hearing aid device 100. The BTE module 300 contains a power source which supplies power to the biometric sensor (s) within the RIC module 200 and to the audio driver 260 within the RIC module 200 via cable 400. The cable 400 may be electrical wiring surrounded by a protective sheath, which may help prevent the electrical wiring from coming in unwanted contact with the body, moisture, or the like.

The BTE module 300 may also include various additional electronic components including, but not limited to, a signal processor, a wireless module for communicating with a remote device, a microphone, a speaker, an environmental sensor, a memory storage device, etc. The power source within the BTE module 300 may be a battery (such as a lithium polymer battery or other portable battery) or other power source sufficiently small to fit within the housing (such as an energy harvesting source). The power source may be charged via a charge port, such as a USB charge port, for example. In some embodiments, the BTE module 300 may include at least one biometric sensor, such as a PPG sensor, ECG sensor, inertial sensor, auscultatory sensor, or the like. In some embodiments, the BTE module 300 may include at least one sensor, such as a physiological (biometric) sensor, an environmental sensor, a motion sensor, or the like. Non-limiting examples of physiological (biometric) sensors may include sensors for measuring physiological properties such as vital signs (heart rate, respiration rate, blood pressure, $SpO_2$, core body temperature, brain activity, and the like) or other biometrics. Non-limiting examples of environmental sensors may include an ambient light sensor, humidity sensor, ambient temperature sensor, or the like. Non-limiting examples of motion sensors may include accelerometers, gyroscopes, mechanical motion sensors, bone conduction sensors, Hall-effect sensors, optical sensors, acoustic sensors, or the like.

Figure 5:
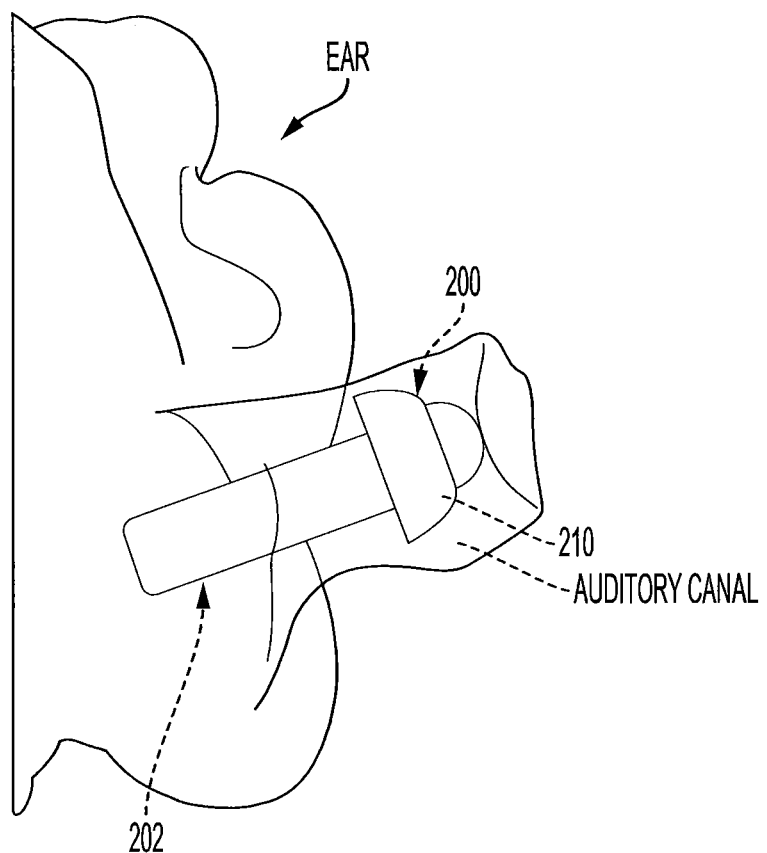
FIG. 5 illustrates the receiver-in-canal ("RIC") module of the hearing aid device of FIG. 4 inserted within an auditory canal of an ear of a person.

The RIC module 200 is configured to be inserted within the auditory canal of an ear of a person, as illustrated in FIG. 5. Referring now to FIGS. 6A-6B, 7-9 and 10A-10C, the RIC module 200 includes a housing 202 having opposite first and second ends 202a, 202b. In the illustrated embodiment, the housing 202 has a generally elongated rectangular shape, although other shapes are possible. As will be described below, the housing 202 contains an optical sensor module 240, a light guide assembly 250, and an audio driver 260 for providing sound to the wearer of the hearing aid device 100. The housing first end 202a includes an elongated, generally cylindrical nozzle 204 extending outwardly therefrom that serves as a sound port. The nozzle 204 includes an acoustic passage 206 that is configured to direct sound from the audio driver 260 within the housing 202 to the ear of a wearer. In the illustrated embodiment, the acoustic passage 206 extends along a longitudinal centerline C (FIG. 9) of the housing 202. In other embodiments, the nozzle 204 may be configured such that at least a portion of the acoustic passage 206 extends along a non-centerline portion of the housing 202.

An ear tip 210 is coupled to the nozzle 204 of the housing 202 and, in the illustrated embodiment, includes a body member 212 having opposite first and second ends 212a, 212b, and an acoustic passage 214 extending therethrough from the first end 212a to the second end 212b. A flange 216 having a generally conical or hemispherical shape extends outwardly over the body member 212 from the body member first end 212a, as illustrated. The flange includes opposite outer and inner surfaces 216a, 216b. The ear tip 210 is configured to comfortably retain the RIC module 200 within a user's auditory canal and, optionally, to substantially seal the auditory canal to attenuate external sounds and to provide a secure fit. The ear tip 210 is formed of a soft, conformable material, such as silicone, and may have a substantially uniform wall thickness between the inner surface 216b (FIG. 4) and the outer surface 216a. However, variable wall thicknesses may be utilized in some embodiments. Material for the ear tip 210 is not limited to silicone; various other soft, thermoplastic elastomers may be used, also. Although a hard ear tip 210 may be used with embodiments of the present invention, a non-compliant ear tip 210 may generate a pain response in the person wearing the device.

In some embodiments, the ear tip 210 is designed to be replaceable and can be removably secured to the nozzle 204 of the housing 202 such that a user can select and use an ear tip 210 that best fits the ear of the user. In the illustrated embodiment, the nozzle 204 is inserted within a receiving channel 212c of the ear tip body member 212. The ear tip 210 may be secured to the nozzle 204 via a snug fit of the nozzle 204 within the receiving channel 212c. In other embodiments, a snap fit configuration or other interlocking geometry between the nozzle 204 and the receiving channel 212c may be utilized.

In some embodiments the housing 202 is a plastic housing made from polycarbonate or a reinforced plastic such as a glass filled polyarylamide (e.g., IXEF® brand polyarylamide available from Solvay Group of Belgium). However, the housing 202 may be formed from various other materials. For example, the housing 202 may be formed from a metal or metallic material.

In the illustrated embodiment, the housing 202 includes a front section 220 and a rear section 222 configured to be secured together. The front section has a generally rectangular cross-sectional shape with opposite first and second sides 220a, 220b, opposite third and fourth sides 220c, 220d, and end portion 220e. The rear section 222 has a generally rectangular cross-sectional shape with opposite first and second sides 222a, 222b, opposite third and fourth sides 222c, 222d, and end portion 222e. The cable 400 enters the housing 202 via the end portion 222e in the illustrated embodiments.

The front section 220 includes a pair of openings 230, 232 in opposing sides 220a, 220b thereof that are configured to expose respective light guides 252, 256 located within the housing 202. In the illustrated orientation of the housing front section 220, one opening 230 is facing upwardly and the other opening 232 is facing downwardly.

An optical sensor module 240 is located within the housing 202 and includes a printed circuit board (PCB) 241 that supports a pair of optical emitters 242a, 242b and an optical detector 244 on one side and an accelerometer 246 on the opposite side. The active region of the illustrated optical detector is indicated as 245. Each optical emitter 242a, 242b may be one or more light-emitting diodes (LED), laser diodes (LD), compact incandescent bulbs, micro-plasma emitters, IR blackbody sources, organic LEDs, or the like. The optical detector 244 may be one or more photodiodes, photodetectors, phototransistors, thyristors, solid state devices, optical chipsets, or the like.

Embodiments of the present invention are not limited to the illustrated configuration of the optical sensor module 240. Various numbers of optical emitters, optical detectors, and motion sensors (e.g., accelerometers and the like), as well as other electronics, may be utilized in accordance with embodiments of the present invention. Moreover, various arrangements of optical emitters, optical detectors, and motion sensors on the PCB 241 may be utilized. For example, FIG. 11A illustrates an optical sensor module 240 with a single optical emitter 242a and a single optical detector 244. FIG. 11B illustrates the optical sensor module 240 of FIG. 8 with two optical emitters 242a, 242b.

A light guide assembly 250 is located within the housing 202 adjacent the optical sensor module 240. The light guide assembly 250 includes a pair of first and second light guides 252, 256 and an opaque barrier 259. The first light guide 252 is configured to guide light from the optical emitters 242a, 242b into the skin of the auditory canal of a wearer of the device 100 in a non-line of sight manner. The second light guide 256 is configured to collect light from the skin of the auditory canal of a wearer of the device 100 and direct the collected light to the active region 245 of the optical detector 244 in a non-line of sight manner. The opaque barrier 259 is configured to prevent light from the optical emitters 242a, 242b from directly reaching the optical detector 244 (i.e., crosstalk). The opaque barrier 259 may comprise a material that is opaque and/or reflective in nature: a dark material with roughened surface, a metallic material, a dark or reflective coating, or the like. The opaque barrier 259 may be comprised of a reasonably solid material (such as plastic, acrylic, putty, wax, silicone, polycarbonate, glass, metal, semi-metal, or the like) for which light at the optical emission wavelength(s) cannot pass through.

The first and second light guides 252, 256 each have a flat configuration that allows them to fit closely against or near respective sides 260a, 260b of the audio driver 260 and thereby conserve space. In some embodiments, one or both of the first and second light guides 252, 256 may be supported by the audio driver 260. However, in other embodiments, one or both of the first and second light guides 252, 256 may be supported by the housing 202 or one or more other components and, thus, do not contact the audio driver 260.

Figure 10A:
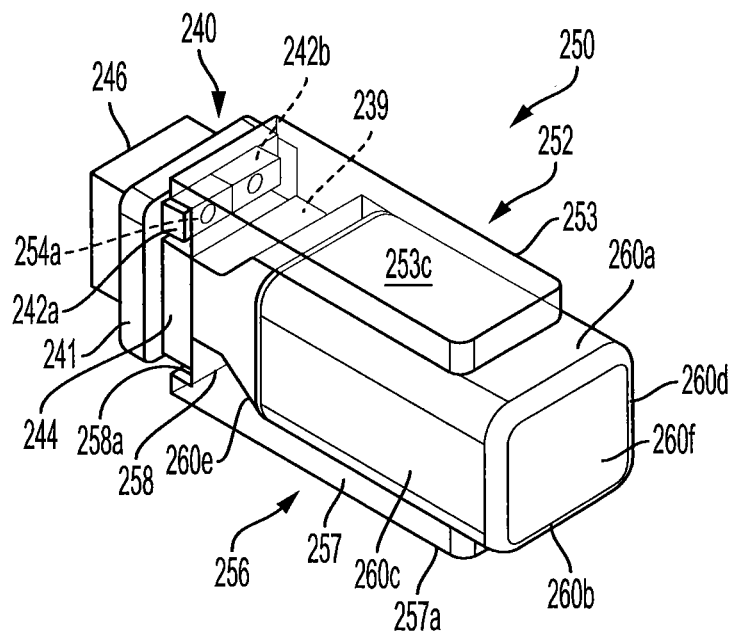
FIG. 10A is a front perspective view of the components housed within the housing of the RIC module of FIGS. 6A-6B.
Figure 10B:
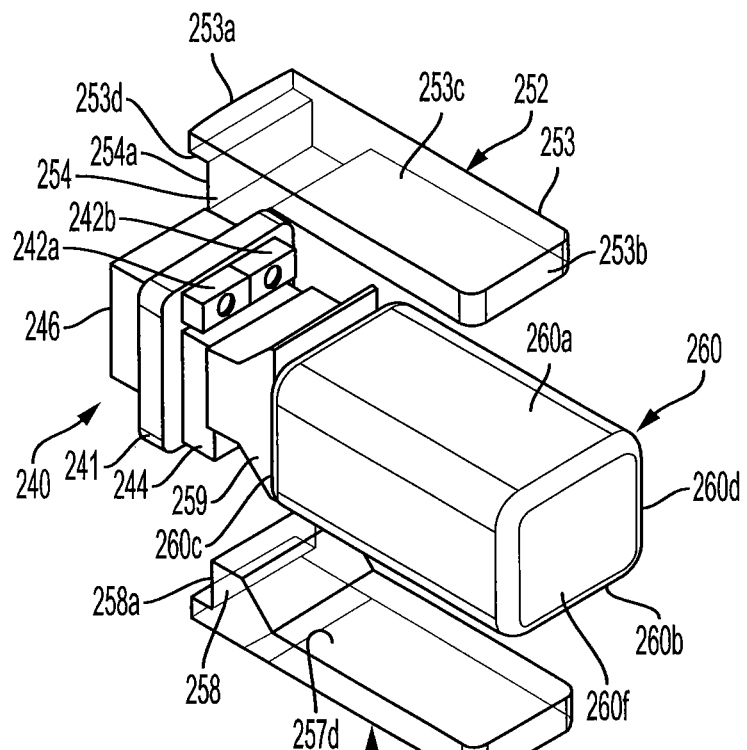
FIGS. 10B-10C are exploded perspective views of the components illustrated in FIG. 10A.
Figure 10C:
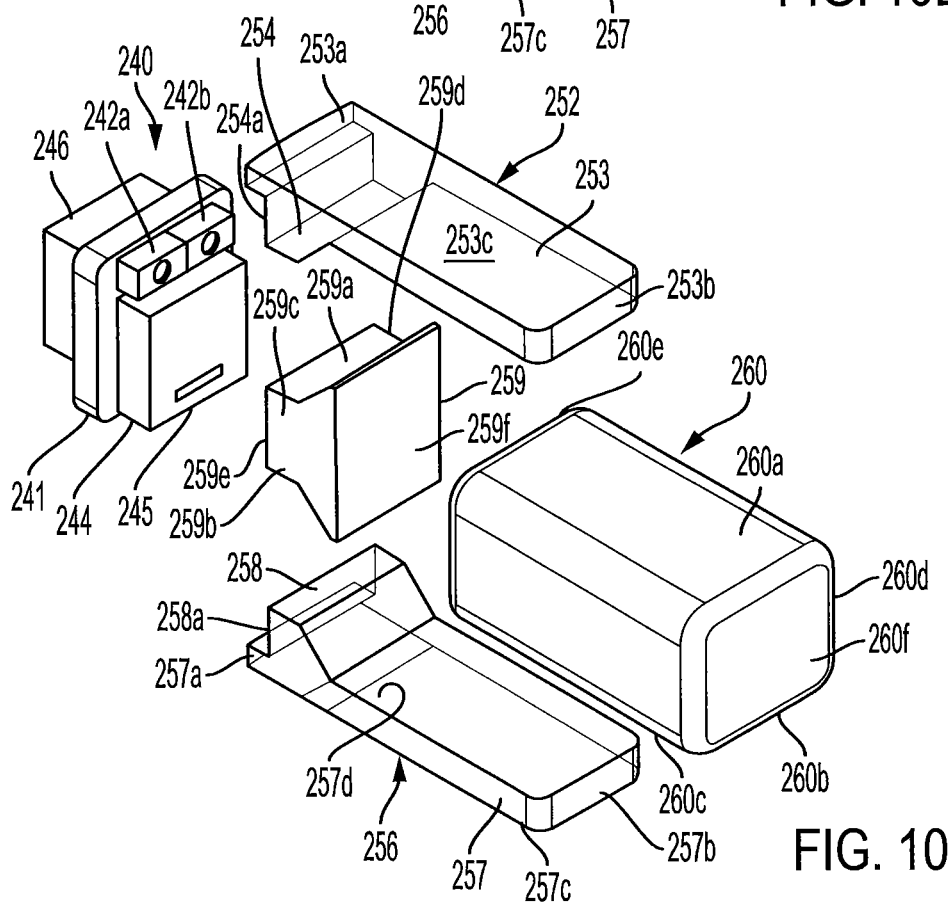
Figure 13:
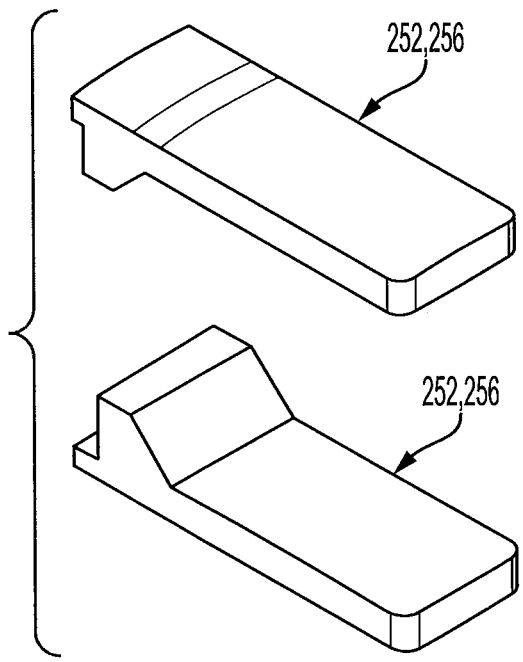
FIGS. 13-22 are perspective views of various configurations and shapes of the light guides utilized in the RIC module of FIGS. 6A-6B, according to some embodiments of the present invention.
Figure 14:
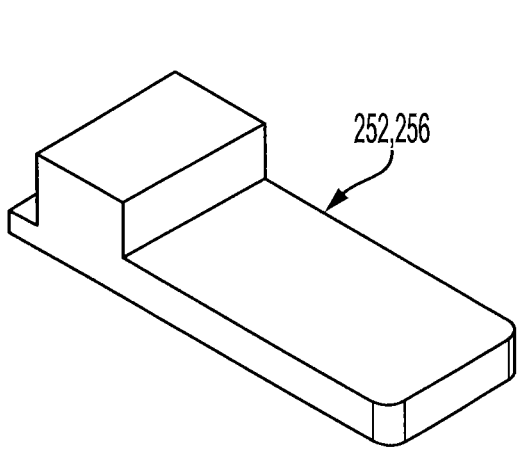
Figure 15:
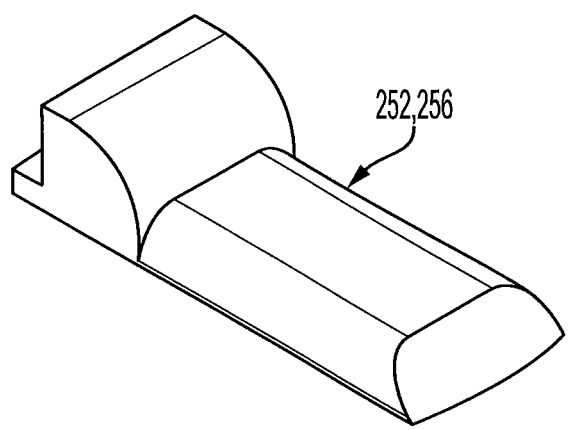
Figure 16:
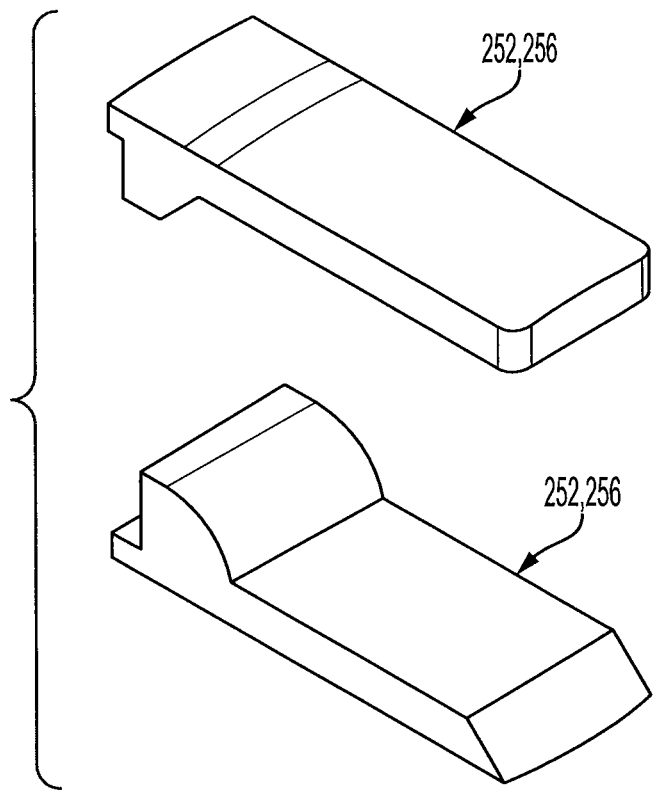
Figure 17:
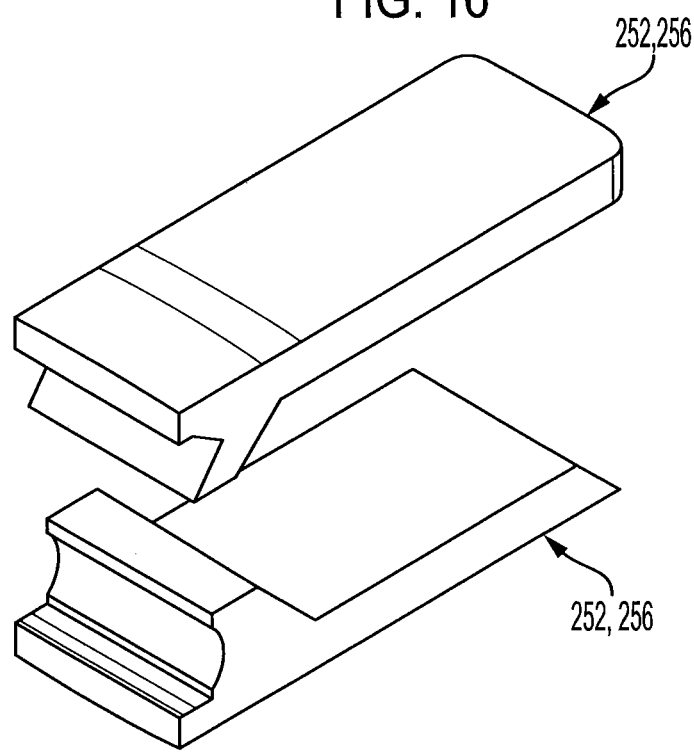
Figure 18:
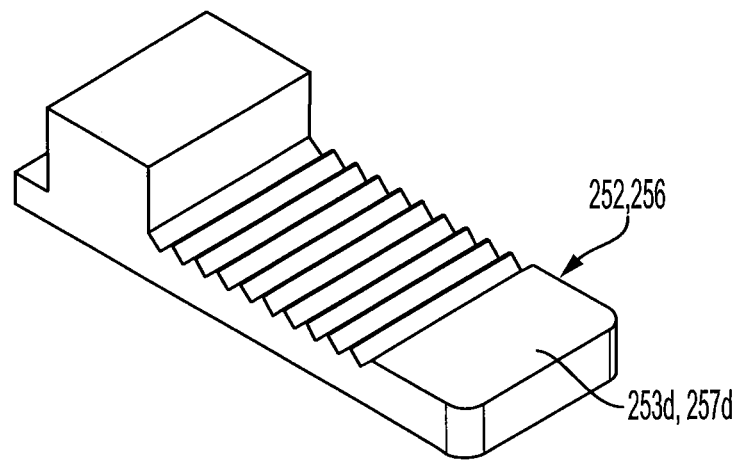
Figure 19:
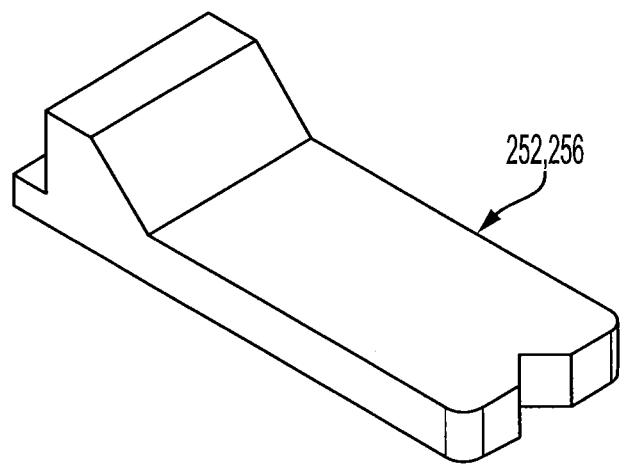
Figure 20:
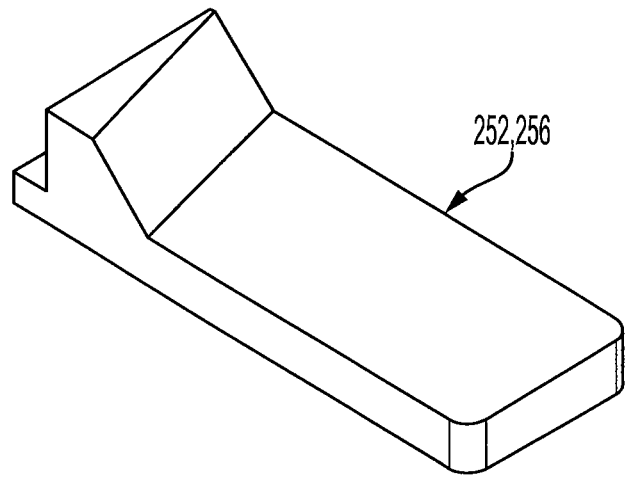
Figure 21:
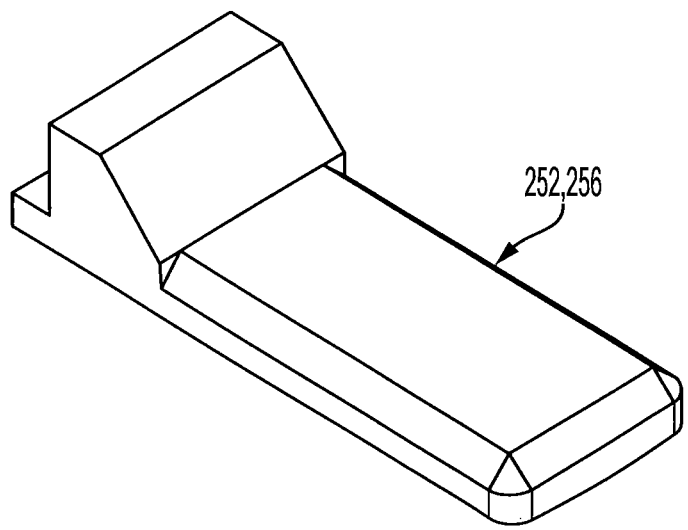
Figure 22:
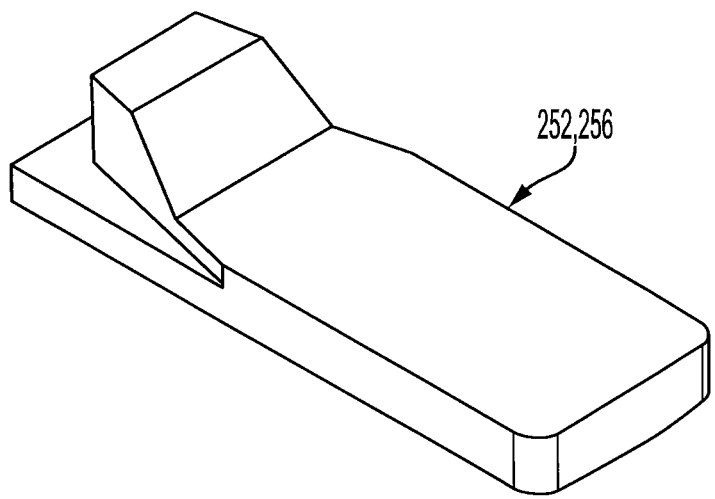

The illustrated opaque barrier 259 has opposite first and second sides 259a, 259b, opposite third and fourth sides 259c, 259d, and opposite first and second end portions 259e, 259f. The first end portion 259e of the opaque barrier 259 is configured to abut or be positioned closely to the optical sensor module 240, and the second end portion 259f of the opaque barrier 259 is configured to abut or be positioned closely to an end portion 260e of the audio driver 260. The opaque barrier first side 259a abuts or is positioned closely to the second section 254 of the first light guide 252, and the opaque barrier second side 259b abuts or is positioned closely to the second section 257 of the second light guide 257 as illustrated in FIG. 10A. The first and second sides 259a, 259b of the opaque barrier 259 can have mating configurations with the respective second sections 254, 258 of the first and second light guides 252, 256. As such, the light guides 252, 256, opaque barrier 259 and audio driver 260 can be assembled compactly with very little wasted space.

The first light guide 252 includes first and second sections 253, 254. The first section 253 has an elongated flat, rectangular configuration with opposite first and second ends 253a, 253b and opposite first and second surfaces 253c, 253d. The second section 254 extends outwardly from the second surface 253d of the first section 253 adjacent the first end 253a of the first section 253. When the optical sensor module 240 and light guide assembly 250 is assembled within the housing 202, a surface 254a of the second section 254 of the first light guide 252 is configured to be positioned near the optical emitters 242a, 242b so as to receive light from the optical emitters 242a, 242b. The first surface 253c of the first section of the first light guide 252 has an elongated flat configuration configured to direct light from the optical emitters 242a, 242b toward the skin of an auditory canal of a wearer of the device 100. Thus, light from the optical emitters 242a, 242b enters the first light guide 252 at surface 254a, passes through the second section 254 into the first section 253, and then exits through the first surface 253c of the first section 253.

The second light guide 256 includes first and second sections 257, 258. The first section 257 has an elongated flat, rectangular configuration with opposite first and second ends 257a, 257b and opposite first and second surfaces 257c, 257d. The second section 258 extends outwardly from the second surface 257d of the first section 257 adjacent the first end 257a of the first section 257. When the optical sensor module 240 and light guide assembly 250 is assembled within the housing 202, a surface 258a of the second section 258 of the second light guide 252 is configured to be positioned near the active region 245 of the optical detector 244. The first surface 257c of the first section 257 of the second light guide 256 has an elongated flat configuration configured to collect light from the skin of an auditory canal of a person wearing the device 100. Thus, light collected by the first surface 257c of the first section 257 passes through the first section 257 into the second section 258 and into the active region 245 of the optical detector 244 via the surface 258a of the second section 258.

FIGS. 13-22 illustrate different configurations that the first and second light guides 252, 256 can have. For example, the first and second sections 253, 254 of the first light guide 252 and the first and second sections 257, 258 of the second light guide 256 can have various shapes and configurations that can be used to change how light is directed from the optical emitters 242a, 242b and to the optical detector 244. In addition, the edges of the first and second light guides 252, 256 can have various shapes and configurations that can be used to change how light is directed from the optical emitters 242a, 242b and to the optical detector 244. In some embodiments, the first and second light guides 252, 256 may have identical configurations. In other embodiments, the first and second light guides 252, 256 may have different configurations.

Furthermore, various surface coatings and finishes, such as textured surfaces and polished surfaces, can be utilized to change the index of refraction or surface reflectivity to further direct or disperse light as desired. For example, the light receiving surface 257c of the second light guide 256 may be smooth, whereas the light guiding surface 253c of the first light guide 252 may have be smooth or texturized or may have a combination of smooth and texturized. Having a texturized surface 253c, 257c may be helpful in guiding light evenly along the periphery of the respective first and second light guides 252, 256. For example, a roughened surface may help scatter light more evenly across the surface.

In some embodiments, the second surface 253d, 257d of one or more of the first and second light guides 252, 256 may be textured. For example, in FIG. 18, the second surface 253d, 257d has a saw tooth configuration. Such a saw tooth pattern can help to generate a desirable optical beam shape or to guide light in a desirable direction. Alternatively, a microlens array may be integrated on the light guide surfaces 253d, 257d to facilitate optical beam shaping and/or light guiding. Alternatively, the light guides 252, 256 may comprise photonic crystalline structures or photonic metamaterials to facilitate optical beam shaping and/or light guiding.

The audio driver 260 is in acoustic communication with the acoustic passage 206 of the nozzle 204 and with the acoustic passage 214 of the ear tip 210 and is configured to deliver sound to the wearer of the device 100. The illustrated audio driver 260 has a generally elongated rectangular cross-sectional configuration with opposite first and second sides 260a, 260b, opposite third and fourth sides 260c, 260d, and opposite end portions 260e, 260f. The audio driver 260 typically has a sound outlet tube extending outward from a sound port (not shown) in end portion 260f which is in acoustic communication with the acoustic passage 206 of the nozzle 204 and with the acoustic passage 214 of the ear tip 210. However, audio drivers that may be utilized in accordance with embodiments of the present invention may have various shapes and configurations and are not limited to the illustrated shape/configuration.

The audio driver 260 may be mounted within the housing 202 in various ways. In some embodiments, the audio driver 260 is secured to the housing front section 220. In other embodiments, the audio driver 260 may mounted within the housing 202 in a flexible jacket or other resilient structure. Such an embodiment may help prevent or reduce vibrations to the audio driver 260. In other embodiments, the audio driver 260 may be mounted on a flexible tube that connects the audio driver 260 to the nozzle 204. Such an embodiment may also help prevent or reduce vibrations to the audio driver 260.

Non-limiting exemplary audio drivers that may be utilized with embodiments of the present invention are available from Sonion, Roskilde, Denmark.

In some embodiments, at least a portion of the audio driver 260, optical emitters 242a, 242b, and optical detector 244 are encapsulated within a hydrophobic encapsulant material.

In some embodiments, an optical filter may be integrated within one or more of the first and second light guides 252, 256. For example, a light guide 252, 256 may comprise a material having an optically filtering dye or a material which inherently filters one or more wavelengths of light. As one example, either or both of the first and second light guides 252, 256 may comprise, wholly or partially, a dye therewithin. As one specific example, a dye, such as an infrared dye designed to block visible wavelengths but pass IR wavelengths may be utilized. For example, a polycarbonate or acrylic light guide 252, 256, dyed with Filtron® absorptive dye E800 (Gentex Corporation, Carbondale, PA), would facilitate both light-guiding and IR-pass filtering functionality. Alternatively, another example of such an integrated physical optical filter comprises absorptive dyes available from Sabic (Riyadh, Saudi Arabia) dispersed in polycarbonate and/or acrylic to create an edge or long-pass optical filter. At least one of the first and second light guides 252, 256 may be partially or wholly comprised of such a material, thereby facilitating the combinational purpose of light guiding and optical filtering. A few additional non-limiting examples of an inherently filtering material includes sapphire, which absorbs some infrared (IR) wavelengths, glass, which absorbs some ultraviolet (UV) wavelengths, and dyed glass (for which dye combinations can be applied to enable optical filtering that is low-pass, high-pass, band-pass, notching, and the like). However, various types of filtering material may be utilized, without limitation.

In some embodiments, an optical filter may be integrated with the optical emitter(s) 242a, 242b and/or the optical detector 244. For example, a bandpass filter, such as an interference filter or the like, may be disposed on an optical emitter 242a, 242b and/or optical detector 20. Alternatively (or additionally), an optical filter effect may be integrated within the semiconductor material comprising the optical emitter 242a, 242b and/or optical detector 244, such as by depositing alternating optically-transparent layers (such as oxides and/or nitrides), selective ion implantation of certain regions within silicon, or by band-gap engineering within compound semiconductors, such as the AlInGaAs or AlIn-GaN system of semiconductor engineering.

In some embodiments of the present invention, the light-guiding material of one or more of the first and second light guides 252, 256 may comprise polarizing material. Exemplary polarizing material that can be used in accordance with embodiments of the present invention is available from American Polarizers, Inc., Reading, Pennsylvania, as well as Edmund Optics, Barrington, New Jersey A key benefit of a cross-polarizing implementation, where the optical emitter polarizer is configured to be orthogonally polarized with respect to the optical detector polarizer, may be that unwanted specular reflection is attenuated such that the light beam collected by the optical detector comprises a higher percentage of photons that have passed through a blood flow region of the body.

Figure 23A:
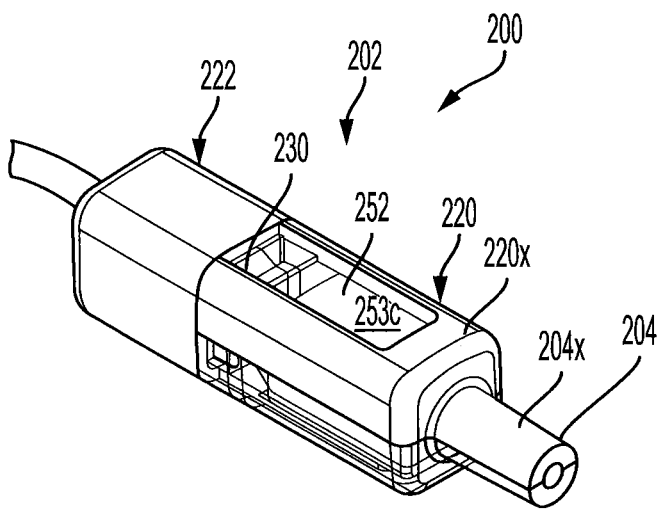
FIG. 23A is a front perspective view of the RIC module of FIGS. 6A-6B with selected portions of the front section of the housing opaque to light, and with a portion of the front section of the housing transparent to light to allow light from the optical emitter to pass therethrough, according to some embodiments of the present invention.

According to embodiments of the present invention, various portions of the housing 202 may be configured to be opaque or transparent in order to improve the signal to noise ratio at the optical detector 244. FIGS. 23A-23F, 24A-24C and 25 illustrate various embodiments of opaque/transparent housing portions. For example, FIG. 23A illustrates the housing 202 of the RIC module 200 of FIGS. 6A-6B with the ear tip removed for clarity and with the portion of the front section 220 near the window 230 for the first light guide 252 opaque as indicated by 220x. In addition, a portion of the nozzle 204 on the same side as the window 230 is opaque as indicated by 204x. As such, only the light leaving the surface 253c of the first light guide 252 illuminates the skin. Light is not allowed to illuminate the skin through the portions of the front section 220 adjacent the first light guide 252. The remainder of the front section 220 and the nozzle 204 remain transparent to light. The rear section 222 of the housing 202 is entirely opaque.

Figure 6A:
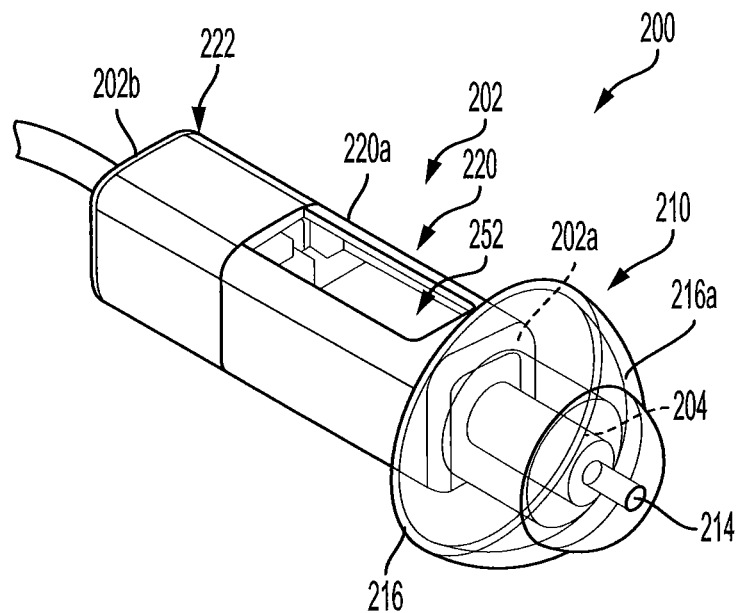
FIGS. 6A and 6B are front perspective views of a RIC module for a hearing aid device according to some embodiments of the present invention.
Figure 6B:
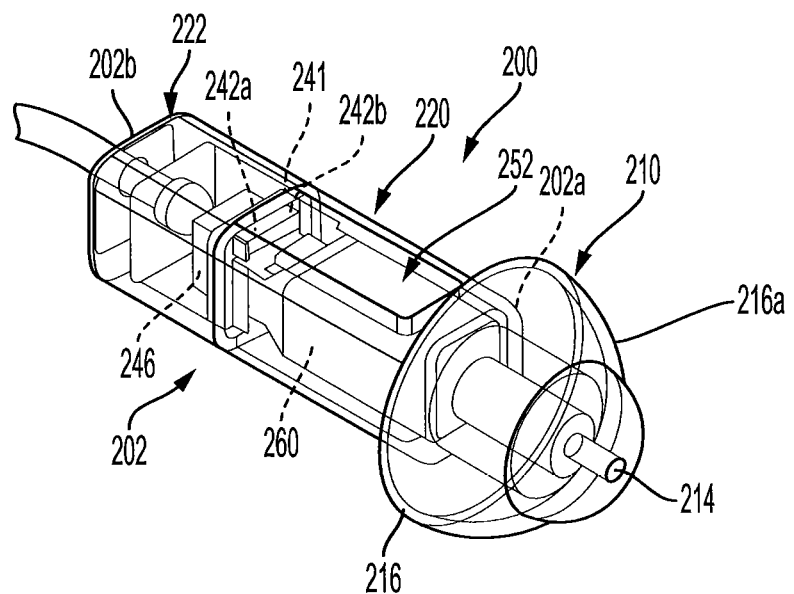
Figure 7:
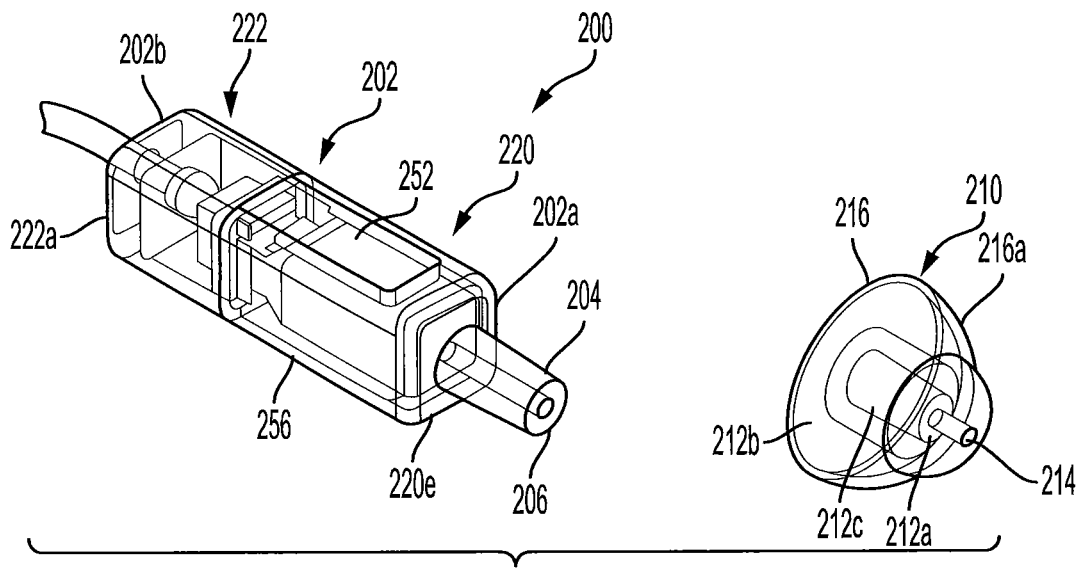
FIG. 7 illustrates the RIC module of FIGS. 6A-6B with the ear tip removed.
Figure 23B:
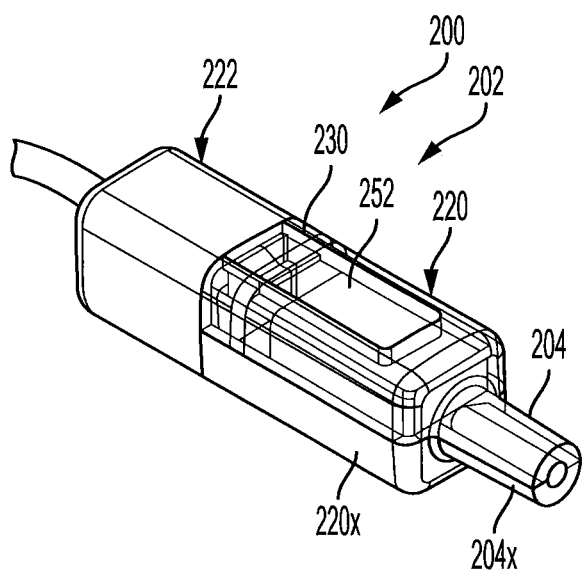
FIG. 23B is a front perspective view of the RIC module of FIGS. 6A-6B with selected portions of the front section of the housing opaque to light, and with selected portions of the front section of the housing transparent to light to allow light from the optical emitter to pass therethrough, according to other embodiments of the present invention.

FIG. 23B illustrates the housing 202 of the RIC module 200 of FIGS. 6A-6B with the ear tip removed for clarity and with the portion of the front section 220 near the window 232 for the second light guide 256 opaque as indicated by 220x. In addition, a portion of the nozzle 204 on the same side as the window 232 is opaque as indicated by 204x. The remainder of the front section 220 and the nozzle 204 remain transparent to light. As such, the entire upper portion of the front section 220 allows light to illuminate the skin. The rear section 222 of the housing 202 is entirely opaque.

Figure 23C:
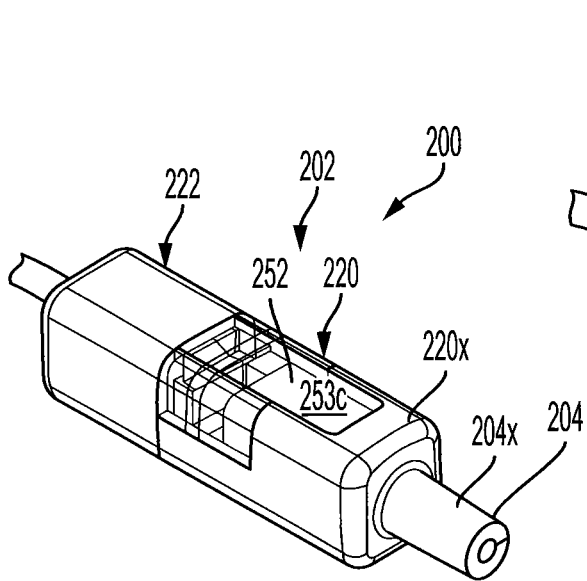
FIG. 23C is a front perspective view of the RIC module of FIGS. 6A-6B with selected portions of the front section of the housing opaque to light, and with selected portions of the front section of the housing transparent to light to allow light from the optical emitter to pass therethrough, according to other embodiments of the present invention.

FIG. 23C illustrates the housing 202 of the RIC module 200 of FIGS. 6A-6B with the ear tip removed for clarity and with the portion of the front section 220 near the window 232 for the second light guide 256 opaque and with selected portions of the front section 220 near the window 230 for the first light guide 252 opaque. The opaque portions of the front section 220 are indicated by 220x. In addition, the entire nozzle 204 is opaque as indicated by 204x. The remaining portions of the front section 220 remain transparent to light. As such, light from the surface 253c of the first light guide 252 and through portions of the front section 220 illuminates the skin. The rear section 222 of the housing 202 is entirely opaque.

Figure 23D:
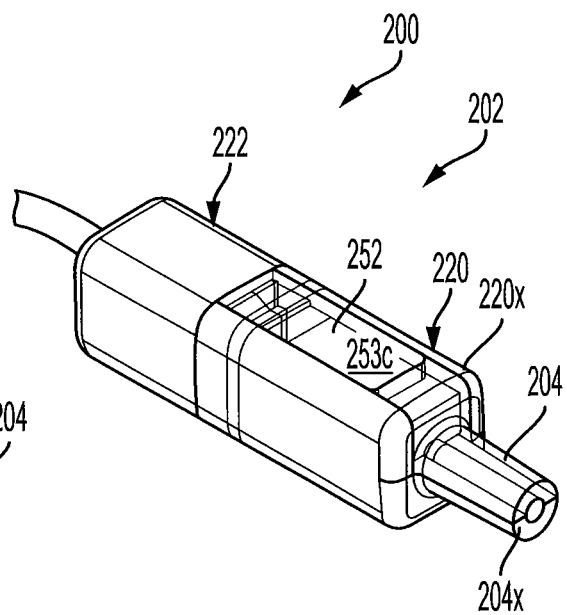
FIG. 23D is a front perspective view of the RIC module of FIGS. 6A-6B with selected portions of the front section of the housing opaque to light, and with selected portions of the front section of the housing transparent to light to allow light from the optical emitter to pass therethrough, according to other embodiments of the present invention.

FIG. 23D illustrates the housing 202 of the RIC module 200 of FIGS. 6A-6B with the ear tip removed for clarity and with the portion of the front section 220 near the window 232 for the second light guide 256 opaque and with selected portions of the front section 220 near the window 230 for the first light guide 252 opaque. The opaque portions of the front section 220 are indicated by 220x. In addition, a portion of the nozzle 204 on the same side as the window 232 is opaque as indicated by 204x. The remaining portion of the front section 220 and the nozzle 204 remain transparent to light. As such, light from the surface 253c of the first light guide 252 and through portions of the front section 220 and nozzle 204 illuminates the skin. The rear section 222 of the housing 202 is entirely opaque.

Figure 23E:
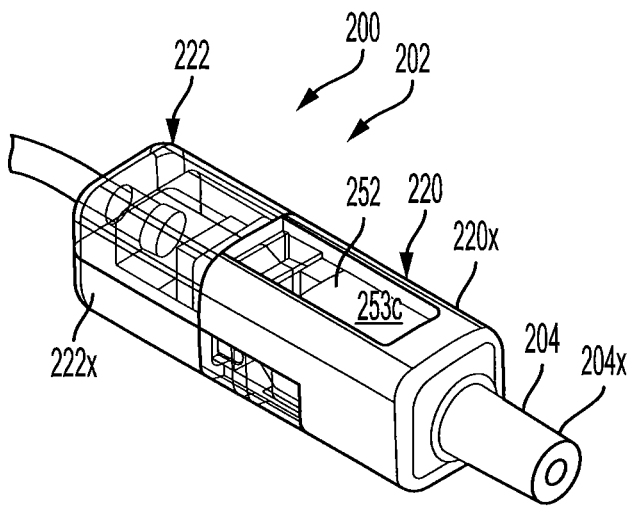
FIG. 23E is a front perspective view of the RIC module of FIGS. 6A-6B with selected portions of the front and rear sections of the housing opaque to light, and with selected portions of the front and rear sections of the housing transparent to light to light to allow light from the optical emitter to pass therethrough, according to other embodiments of the present invention.

FIG. 23E illustrates the housing 202 of the RIC module 200 of FIGS. 6A-6B with the ear tip removed for clarity and with the portion of the front section 220 near the window 230 for the first light guide 252 opaque and with selected portions of the front section 220 near the window 232 for the second light guide 256 opaque. The opaque portions of the front section 220 are indicated by 220x. The entire nozzle 204 is opaque as indicated by 204x. The remaining portions of the front section 220 remain transparent to light. The rear section 222 of the housing 202 has portions that are opaque as indicated by 222x. The remaining portions of the rear section 222 are transparent to light. As such, light from the surface 253c of the first light guide 252 and through the transparent portions of the rear section 222 illuminates the skin.

Figure 23F:
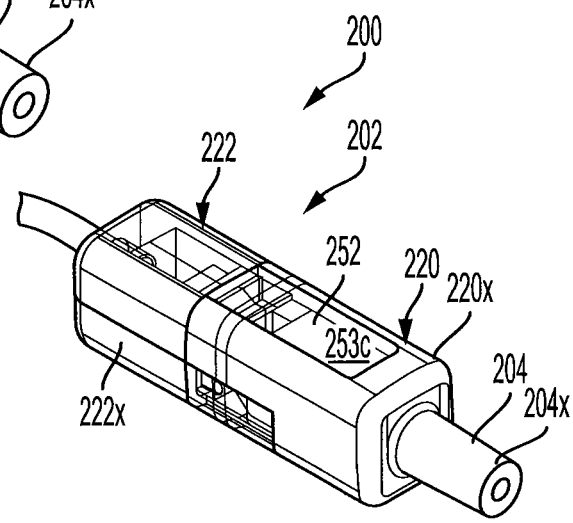
FIG. 23F is a front perspective view of the RIC module of FIGS. 6A-6B with selected portions of the front and rear sections of the housing opaque to light, and with selected portions of the front and rear sections of the housing transparent to light to allow light from the optical emitter to pass therethrough, according to other embodiments of the present invention.

FIG. 23F illustrates the housing 202 of the RIC module 200 of FIGS. 6A-6B with the ear tip removed for clarity and with the portion of the front section 220 near the window 230 for the first light guide 252 opaque and with selected portions of the front section 220 near the window 232 for the second light guide 256 opaque. The opaque portions of the front section 220 are indicated by 220x. The entire nozzle 204 is opaque as indicated by 204x. The remaining portions of the front section 220 remain transparent to light. The rear section 222 of the housing 202 has portions that are opaque as indicated by 222x. The remaining portions of the rear section 222 are transparent to light. As such, light from the surface 253c of the first light guide 252 and through the transparent portions of the rear section 222 illuminates the skin.

Figures 24A, 24B:
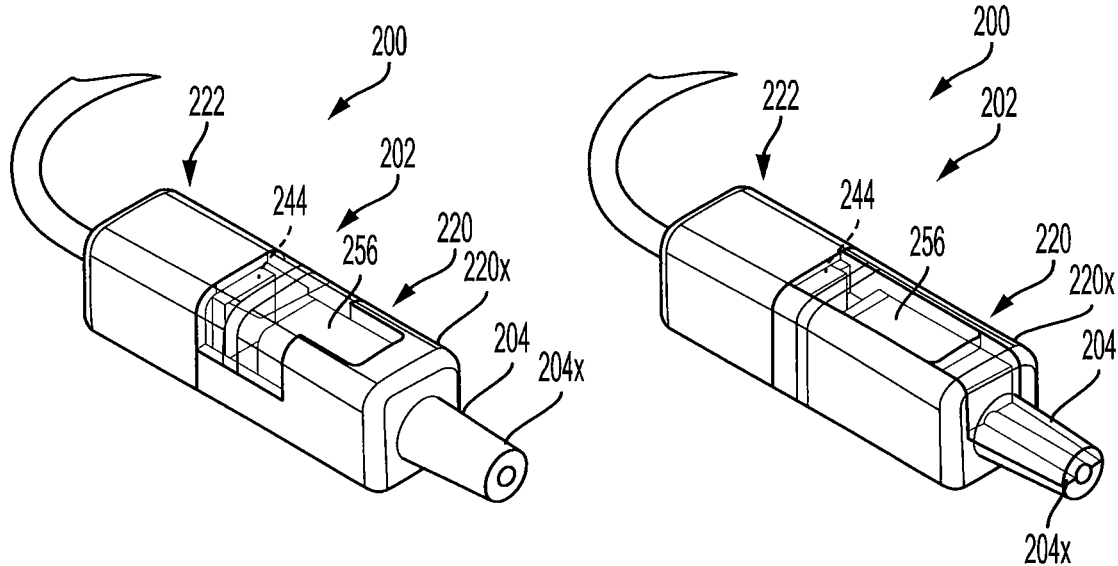
FIG. 24A is a front perspective view of the RIC module of FIGS. 6A-6B with selected portions of the front section of the housing opaque to light, and with selected portions of the front section of the housing transparent to allow light to pass therethrough and reach the optical detector, according to some embodiments of the present invention.
FIG. 24B is a front perspective view of the RIC module of FIGS. 6A-6B with selected portions of the front section of the housing opaque to light, and with selected portions of the front section of the housing transparent to allow light to pass therethrough and reach the optical detector, according to other embodiments of the present invention.

FIG. 24A illustrates the housing 202 of the RIC module 200 of FIGS. 6A-6B with the ear tip removed for clarity and with portions of the front section 220 near the window 232 for the second light guide 256 opaque and with the remaining portion of the front section 220 near the window 230 for the first light guide 252 opaque. The opaque portions of the front section 220 are indicated by 220x. In addition, the entire nozzle 204 is opaque as indicated by 204x. The remaining portion of the front section 220 remains transparent to light. The rear section 222 of the housing 202 is entirely opaque. As such, light can be collected through the second light guide 256 and through the transparent portions of the front section 220.

FIG. 24B illustrates the housing 202 of the RIC module 200 of FIGS. 6A-6B with the ear tip removed for clarity and with portions of the front section 220 near the window 232 for the second light guide 256 opaque and with the remaining portion of the front section 220 near the window 230 for the first light guide 252 opaque. The opaque portions of the front section 220 are indicated by 220x. In addition, a portion of the nozzle 204 on the same side as the window 230 is opaque as indicated by 204x. The remaining portion of the front section 232 and the nozzle 204 remain transparent to light. The rear section 222 of the housing 202 is entirely opaque. As such, light can be collected through the second light guide 256 and through the transparent portions of the front section 220 and nozzle 204.

Figure 24C:
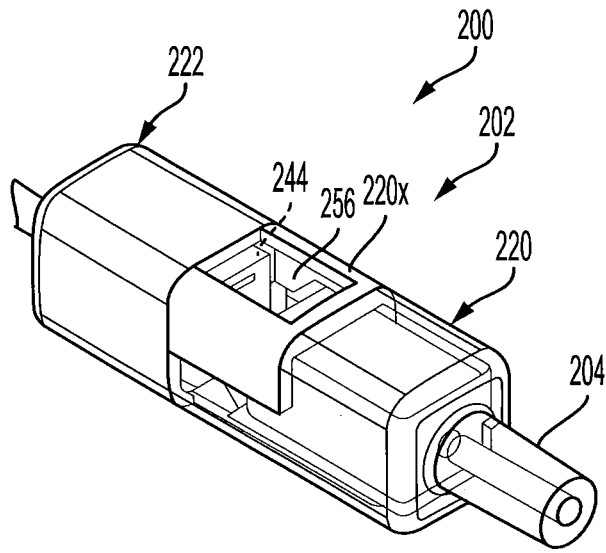
FIG. 24C is a front perspective view of the RIC module of FIGS. 6A-6B with selected portions of the front section of the housing opaque to light, and with selected portions of the front section of the housing transparent to allow light to pass therethrough and reach the optical detector, according to other embodiments of the present invention.

FIG. 24C illustrates the housing 202 of the RIC module 200 of FIGS. 6A-6B with the ear tip removed for clarity and with a portion of the front section 220 near the window 232 for the second light guide 256 opaque as indicated by 220x.

The remaining portions of the front section 220 and the nozzle 204 are transparent to light. The rear section 222 of the housing 202 is entirely opaque. As such, light can be collected through the second light guide 256 and through the transparent portions of the front section 220 and nozzle 204.

Figure 25:
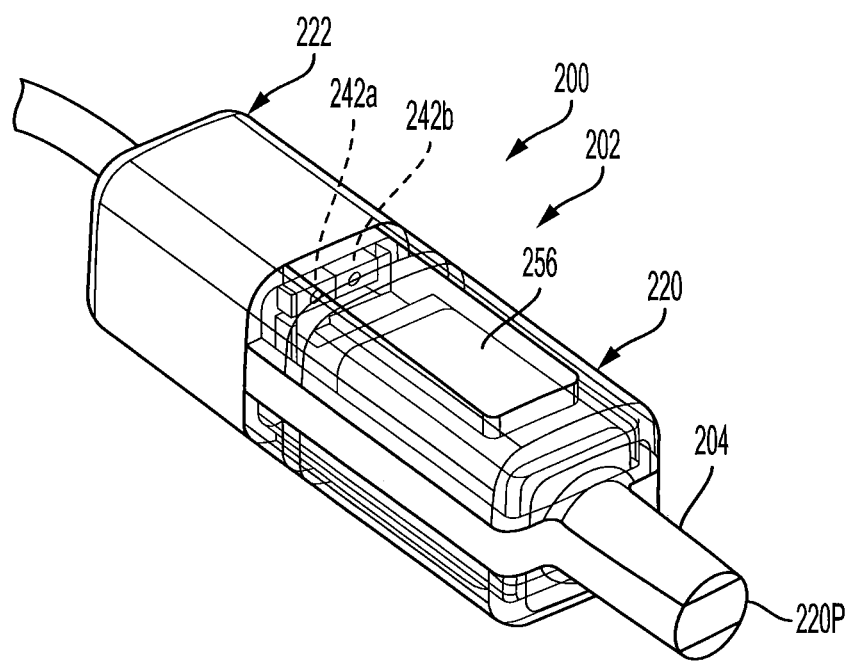
FIG. 25 is a front perspective view of the RIC module of FIGS. 6A-6B with an opaque boundary positioned around a periphery of the front section of the housing to prevent crosstalk between the optical emitter and detector, according to some embodiments of the present invention.

FIG. 25 illustrates the housing 202 of the RIC module 200 of FIGS. 6A-6B with the ear tip removed for clarity and with a peripheral portion of the front section 220 and the nozzle opaque as indicated by 220p. The portion 220p prevents crosstalk between the optical emitters 242a, 242b and the optical detector 244.

Referring back to FIG. 12, in some embodiments, an opaque barrier 247 may extend between the optical emitters 242a, 242b and the optical detector 244. This opaque barrier 247 may be utilized with or without the various opaque housing embodiments described above.

Figure 26:
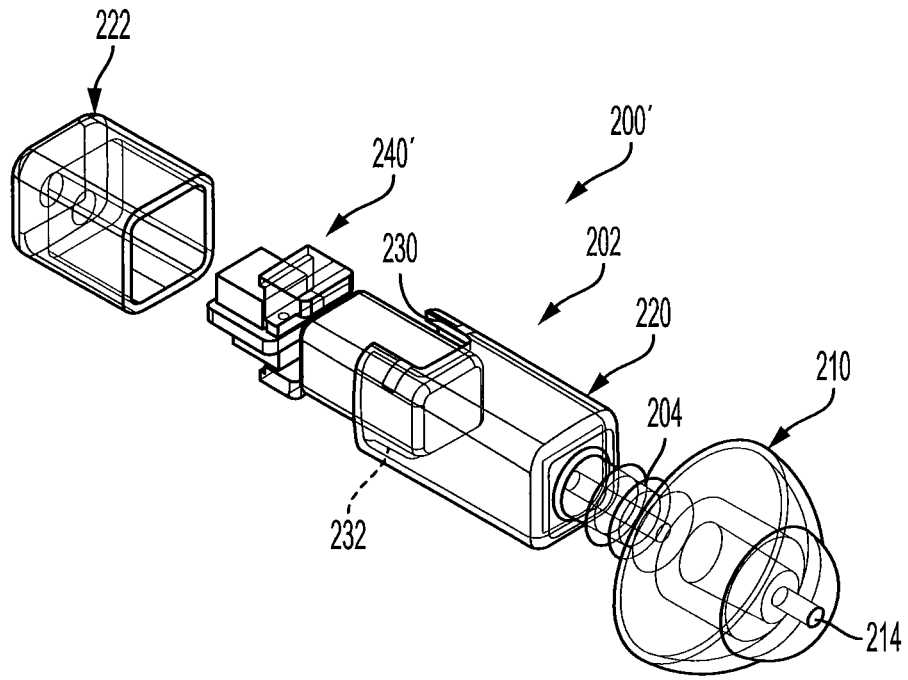
FIG. 26 is an exploded perspective view of a RIC module according to other embodiments of the present invention.
Figure 27:
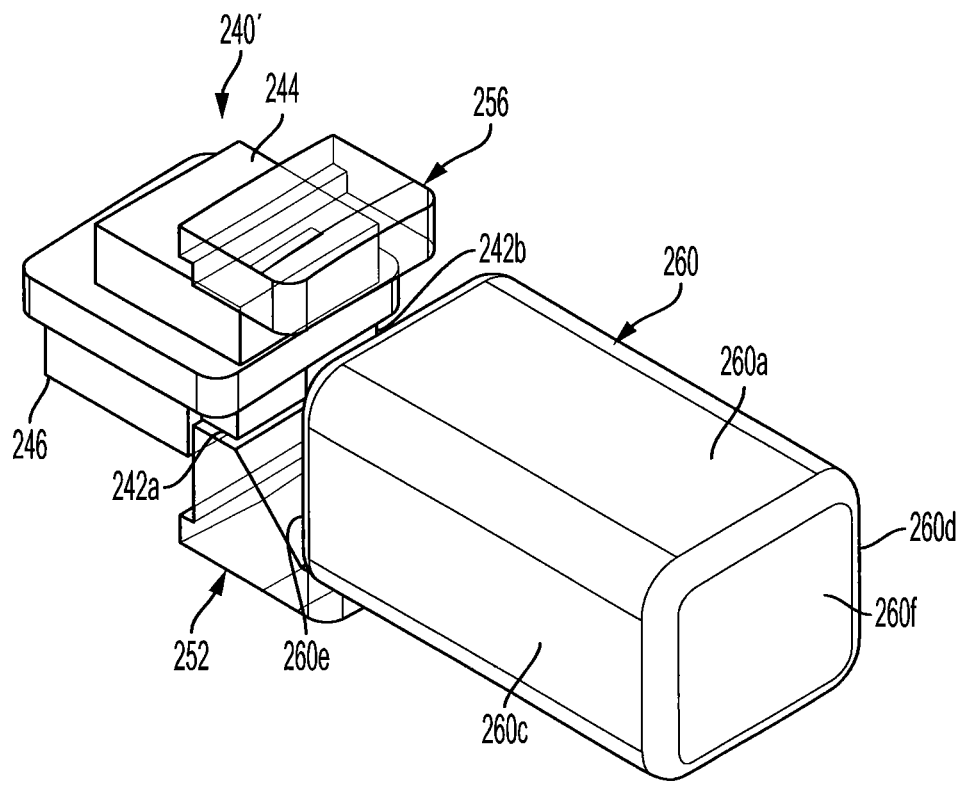
FIG. 27 is a perspective view of the optical sensor module and light guides of FIG. 26, and wherein the optical detector is facing upwardly.
Figure 28:
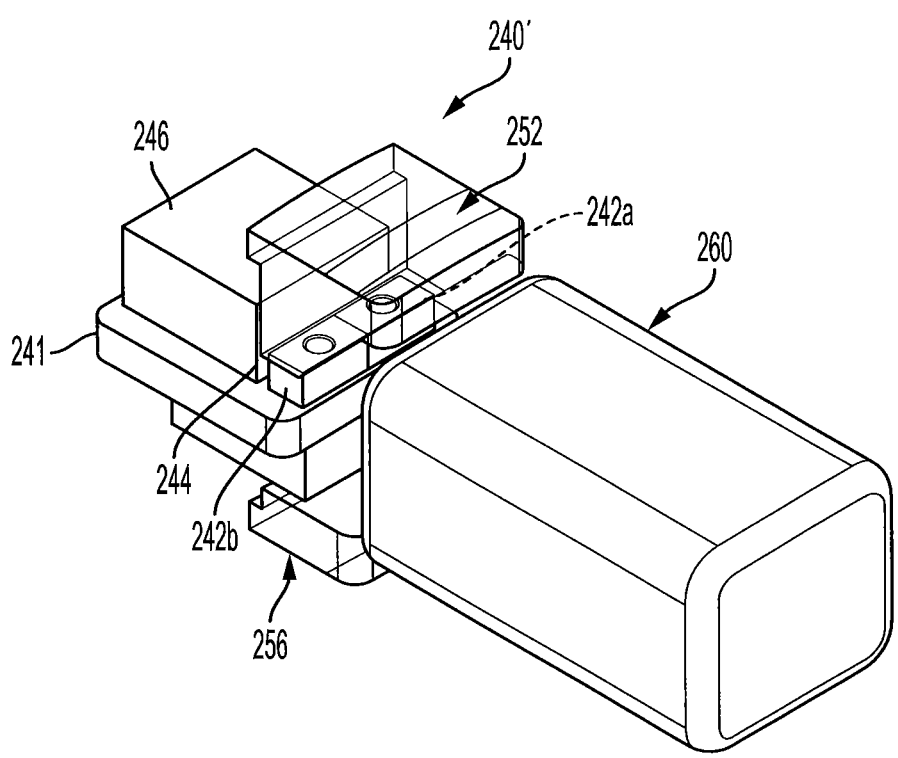
FIG. 28 is a perspective view of the optical sensor module and light guides of FIG. 26, and wherein the optical emitters are facing upwardly.

Referring now to FIGS. 26-28, a RIC module 200' according to other embodiments of the present invention is illustrated. The RIC module 200' includes a housing 202 having a front section 220 and a back section 222. Within the housing are an optical sensor module 240', first and second light guides 252, 256, and an audio driver 260. The illustrated RIC module 200' does not utilize a separate opaque barrier/body. Instead, the optical sensor module 240' is rotated 90° relative to other embodiments such that the optical emitters 242a, 242b face the first opening 230 in the housing front section 220 and such that the active region 245 of the optical detector 244 faces the second opening 232 in the housing front section 220. In this configuration, the PCB 241 serves as an optical barrier to prevent crosstalk between the optical emitters 242a, 242b and the optical detector 244. FIG. 27 illustrates the optical sensor module 240' oriented such that the optical detector 244 is facing upwardly, and FIG. 28 illustrates the optical sensor module 240' oriented such that the optical emitters 242a, 242b are facing upwardly. The orientation of the optical sensor module 240' in FIGS. 26-28 allows for creating a "standard" backend of a RIC module that can be utilized with various front end configurations (i.e., audio driver configurations).

Because the optical emitters 242a, 242b face the first opening 230 the first light guide 252 guides light from the optical emitters 242a, 242b through the opening 230 and into skin of the auditory canal in a line of sight manner. Similarly, because the optical detector 244 faces the second opening 232, the second light guide 256 collects light from the skin of the auditory canal and directs the collected light to the optical detector 244 in a line of sight manner.

The first and second light guides 252, 256 in FIGS. 26-28 have a shorter length than the light guides 252, 256 of previous embodiments because of the orientation of the optical emitters 242a, 242b and optical detector 244. However, it is understood that the light guides 252, 256 in FIGS. 26-28 may be longer than illustrated and may have the same or similar lengths as the light guides 252, 256 in previously illustrated embodiments.

Figure 29:
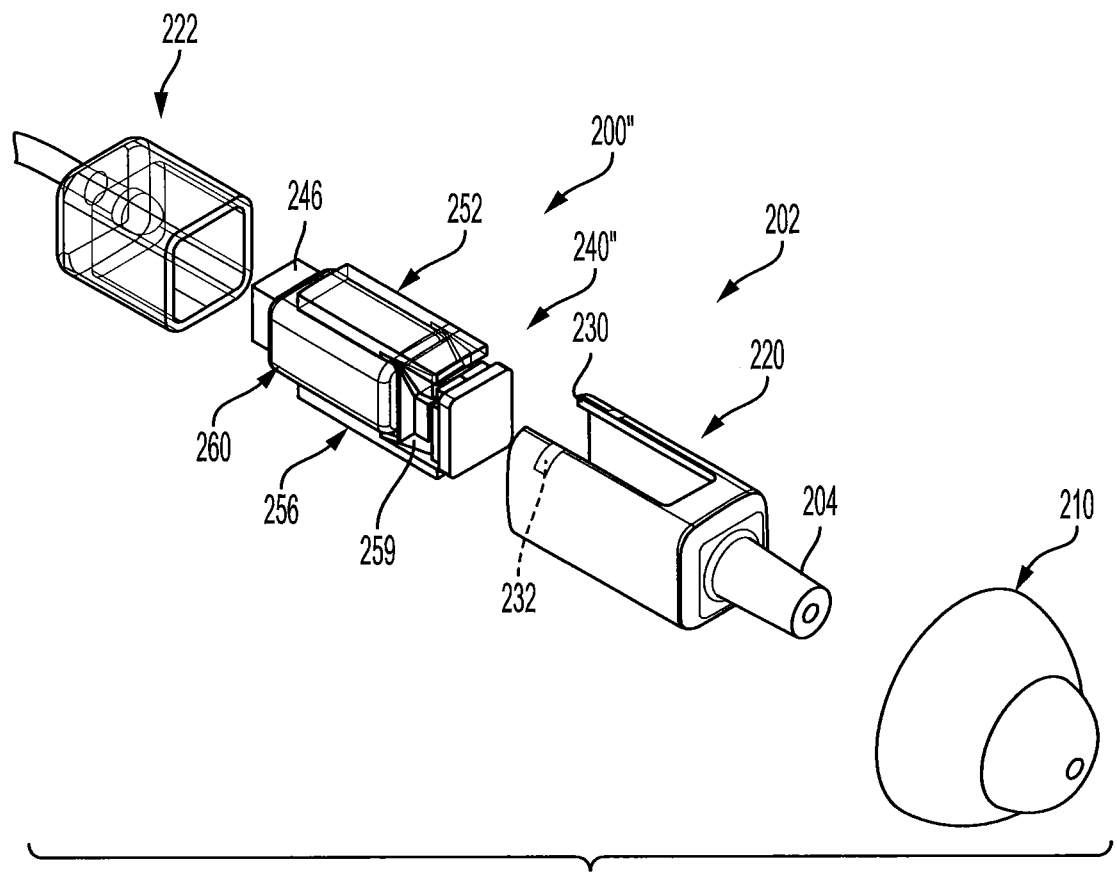
FIG. 29 is an exploded perspective view of a RIC module according to other embodiments of the present invention.
Figure 30:
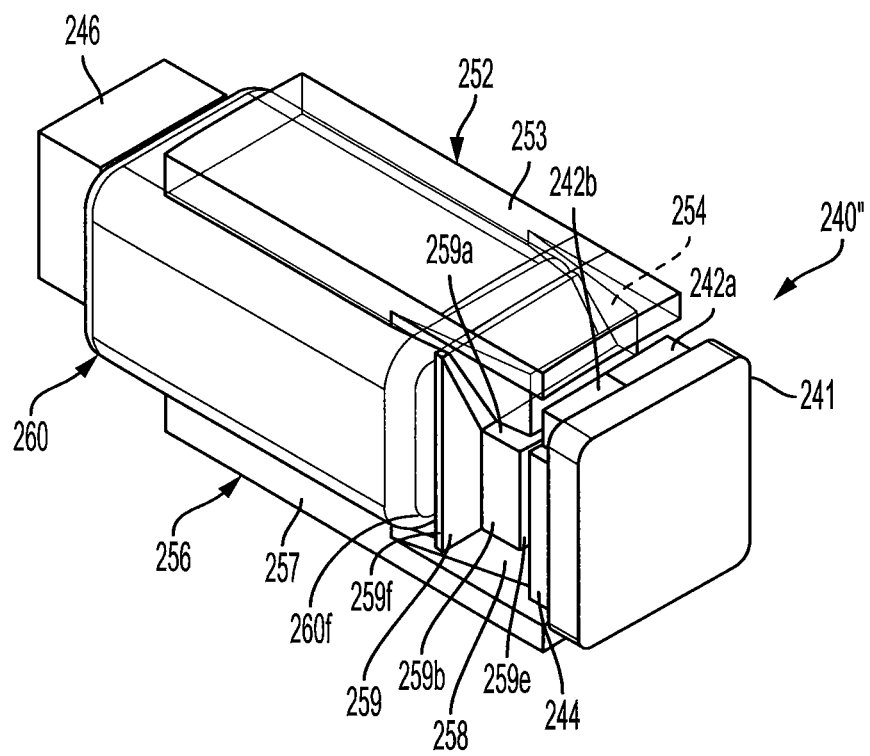
FIG. 30 is a perspective view of the optical sensor module, light guides, and audio driver of FIG. 30.

Referring now to FIGS. 29-30, a RIC module 200" according to other embodiments of the present invention is illustrated. The RIC module 200" is similar to the RIC module 200 illustrated in FIGS. 8 and 10A, except the optical sensor module 240" is positioned at the front end 260f of the audio driver 260, the optical emitters 242a, 242b and optical detector 244 are oriented facing the rear section 222 of the housing (i.e., away from the ear tip 210), and the accelerometer 246 is secured to the rear end 260e of the audio driver 260.

Figure 8:
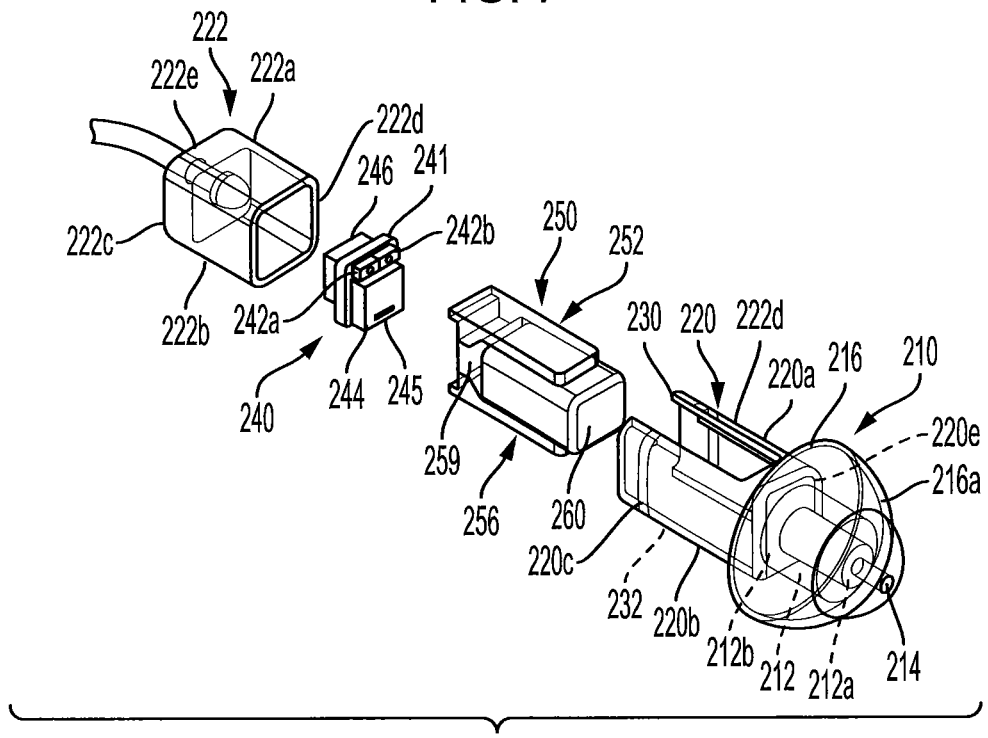
FIG. 8 is an exploded perspective view of the RIC module of FIGS. 6A-6B.
Figure 9:
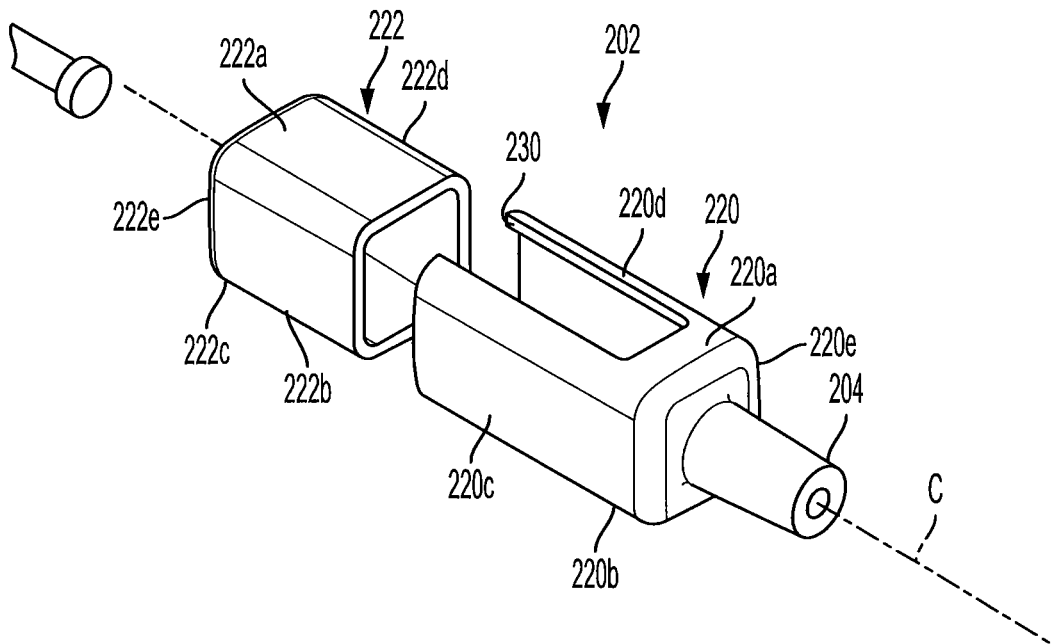
FIG. 9 is an exploded perspective view of the housing of the RIC module of FIGS. 6A-6B illustrating the front section and rear section thereof.

An opaque barrier 259 similar to the one illustrated in FIGS. 8 and 10A is utilized and has opposite first and second sides 259a, 259b and opposite first and second end portions 259e, 259f. The first end portion 259e of the opaque barrier 259 abuts or is positioned closely to the optical sensor module 240", and the second end portion 259f of the opaque barrier 259 abuts or is positioned closely to the front end portion 260f of the audio driver 260. The opaque barrier first side 259a abuts or is positioned closely to the second section 254 of the first light guide 252, and the opaque barrier second side 259b abuts or is positioned closely to the second section of the second light guide 257. As with the embodiment illustrated in FIGS. 8 and 10A, the light guides 252, 256, opaque barrier 259 and audio driver 260 of FIGS. 29 and 30 can be assembled compactly with very little wasted space.

Figure 31:
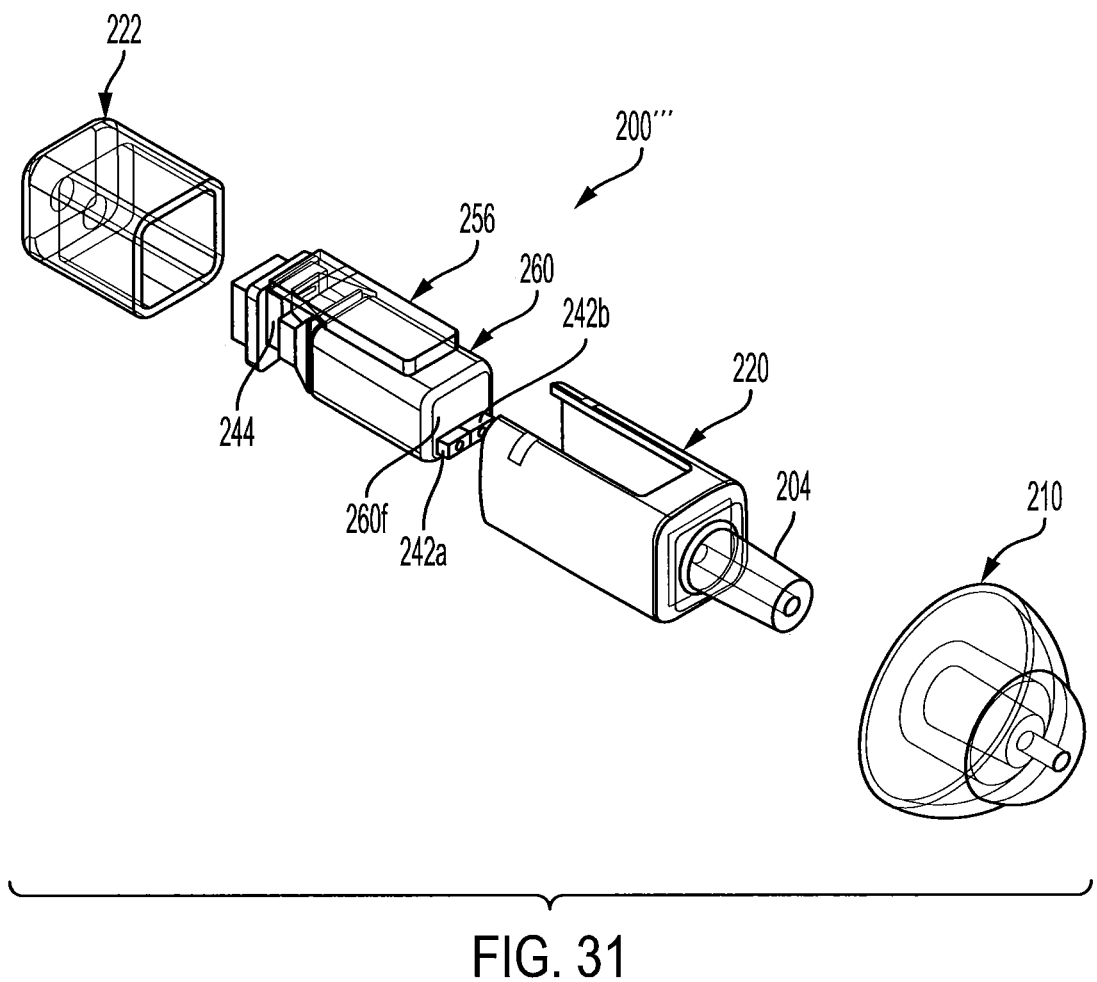
FIG. 31 is an exploded perspective view of a RIC module according to other embodiments of the present invention.
Figure 32:
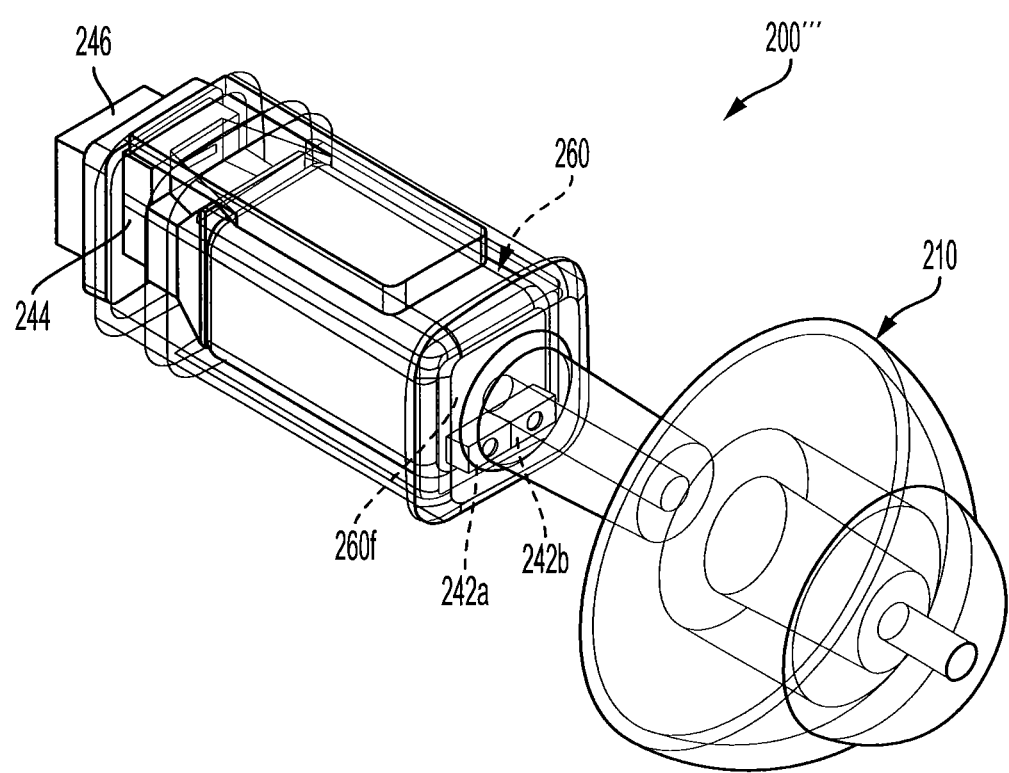
FIG. 32 is a perspective view of the optical sensor module, light guides, audio driver, and ear tip of FIG. 30.

Referring now to FIGS. 31-32, a RIC module 200' according to other embodiments of the present invention is illustrated. The RIC module 200'" is similar to the RIC module 200 illustrated in FIGS. 8 and 10A, except the optical emitters 242a, 242b are positioned on the front end 260f of the audio driver 260 and face forward towards the ear tip 210. The optical detector 244 is mounted on the rear end 260e of the audio driver 260 via an opaque barrier, and a single light guide 256 is utilized to collect light from the skin of the auditory canal and direct the collected light to the active region 245 of the optical detector 244 in a non-line of sight manner, as described above. The nozzle 204 and the ear tip 210 are formed at least partially from light guiding material and serve as a light guide to direct light from the optical emitters 242a, 242b into the skin of the auditory canal.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A hearing aid module configured to be inserted within the auditory canal of an ear of a subject, the module comprising:
    an elongated housing having a rectangular configuration with opposite first and second sides, opposite third and fourth sides, and opposite first and second ends, wherein the first and second sides each comprise an opening, and wherein the housing comprises an acoustic passage through the first end thereof;
    an optical sensor module located within the housing, the optical sensor module comprising at least one optical emitter and at least one optical detector;
    an audio driver positioned within the housing adjacent the optical sensor module, wherein the audio driver is configured to provide sound to the subject via the housing acoustic passage;
    a first light guide positioned within the housing and configured to guide light from the at least one optical emitter through the opening in the housing first side and toward skin of the auditory canal in a non-line of sight manner; and
    a second light guide positioned within the housing and configured to collect light from the skin of the auditory canal and direct the collected light to the at least one optical detector in a non-line of sight manner.

2. The hearing aid module of claim 1, further comprising an opaque body positioned between the optical sensor module and the audio driver, wherein the opaque body is configured to prevent crosstalk between the at least one optical emitter and the at least one optical detector.

3. The hearing aid module of claim 2, wherein the opaque body comprises opposite first and second sides, opposite third and fourth sides, and opposite first and second end portions, wherein the opaque body first end portion is positioned near the optical sensor module, wherein the opaque body second end portion is positioned near an end portion of the audio driver, wherein the opaque body first side is positioned near a portion of the first light guide and wherein the opaque body second side is positioned near a portion of the second light guide.

4. The hearing aid module of claim 2, wherein the opaque body is a part of a housing of the audio driver.

5. The hearing aid module of claim 1, wherein the first light guide comprises first and second sections, wherein the first section has an elongated flat configuration with opposite first and second ends and opposite first and second surfaces, wherein the second section extends outwardly from the second surface of the first section adjacent the first end of the first section, wherein the second section is positioned near the at least one optical emitter, wherein the first section second surface is positioned near a surface of the audio driver, and wherein light from the at least one optical emitter passes into the first light guide through the second section and exits through the first section first surface.

6. The hearing aid module of claim 1, wherein the second light guide comprises first and second sections, wherein the first section has an elongated flat configuration with opposite first and second ends and opposite first and second surfaces, wherein the second section extends outwardly from the second surface of the first section adjacent the first end of the first section, wherein the second section is positioned near the at least one optical detector, wherein the first section second surface is positioned near a surface of the audio driver, and wherein the second light guide collects light from the skin of the auditory canal through the first section first surface and directs the collected light into the at least one optical detector via the second section.

7. The hearing aid module of claim 1, further comprising an ear tip coupled to the housing, wherein the ear tip is configured to retain the module within the auditory canal.

8. The hearing aid module of claim 1, wherein the housing comprises front and rear sections.

9. The hearing aid module of claim 1, wherein portions of the housing adjacent the opening in the housing first side and/or the opening in the housing second side are opaque.

10. A hearing aid device, comprising:
a first module comprising a power supply; and
a second module configured to be inserted within an auditory canal of an ear of a subject, wherein the first and second modules are electrically coupled via a cable, wherein the second module comprises:
an elongated housing having a rectangular configuration with opposite first and second sides, opposite third and fourth sides, and opposite first and second ends, wherein the first and second sides each comprise an opening, and wherein the housing comprises an acoustic passage through the first end thereof;
an optical sensor module located within the housing, the optical sensor module comprising at least one optical emitter and at least one optical detector;
an audio driver positioned within the housing adjacent the optical sensor module, wherein the audio driver is configured to provide sound to the subject via the acoustic passage;
a first light guide positioned within the housing and configured to guide light from the at least one optical emitter through the opening in the housing first side and toward skin of the auditory canal in a non-line of sight manner; and
a second light guide positioned within the housing and configured to collect light from the skin of the auditory canal and direct the collected light to the at least one optical detector in a non-line of sight manner.

11. The hearing aid device of claim 10, wherein the first module is adapted to be disposed behind the ear of the subject during operation of the hearing aid device.

12. The hearing aid device of claim 10, further comprising an opaque body positioned between the optical sensor module and the audio driver, wherein the opaque body is configured to prevent crosstalk between the at least one optical emitter and the at least one optical detector.

13. The hearing aid device of claim 12, wherein the opaque body comprises opposite first and second sides, opposite third and fourth sides, and opposite first and second end portions, wherein the opaque body first end portion is positioned near the optical sensor module, wherein the opaque body second end portion is positioned near an end portion of the audio driver, wherein the opaque body first side is positioned near a portion of the first light guide, and wherein the opaque body second side is positioned near a portion of the second light guide.

14. The hearing aid device of claim 12, wherein the opaque body is a part of a housing of the audio driver.

15. The hearing aid device of claim 10, wherein the first light guide comprises first and second sections, wherein the first section has an elongated flat configuration with opposite first and second ends and opposite first and second surfaces, wherein the second section extends outwardly from the second surface of the first section adjacent the first end of the first section, wherein the second section is positioned near the at least one optical emitter, wherein the first section second surface is positioned near a surface of the audio driver, and wherein light from the at least one optical emitter passes into the first light guide through the second section and exits through the first section first surface.

16. The hearing aid device of claim 10, wherein the second light guide comprises first and second sections, wherein the first section has an elongated flat configuration with opposite first and second ends and opposite first and second surfaces, wherein the second section extends outwardly from the second surface of the first section adjacent the first end of the first section, wherein the second section is positioned near the at least one optical detector, wherein the first section second surface is positioned near a surface of the audio driver, and wherein the second light guide collects light from the skin of the auditory canal through the first section first surface and directs the collected light into the at least one optical detector via the second section.

17. The hearing aid device of claim 10, further comprising an ear tip coupled to the housing, wherein the ear tip is configured to retain the module within the auditory canal.

18. The hearing aid device of claim 10, wherein the housing comprises front and rear sections.

19. The hearing aid device of claim 10, wherein portions of the housing adjacent the opening in the housing first side and/or the opening in the housing second side are opaque.

* * * * *